US012419845B1

(12) United States Patent
Dahiya et al.

(10) Patent No.: US 12,419,845 B1
(45) Date of Patent: Sep. 23, 2025

(54) METHODS FOR TREATING NEURODEVELOPMENTAL DISORDERS VIA ADMINISTRATION OF ORGANIC TRICYCLIC COMPOUNDS

(71) Applicant: Syngap Research Fund, San Diego, CA (US)

(72) Inventors: Marta Dahiya, Arlington, TX (US); Mike Graglia, Mill Valley, CA (US); Drishti Guin, Oakland, CA (US); Kathryn Helde, Seattle, WA (US); Chris Moxham, Palo Alto, CA (US); Sabine Topka, Mountain View, CA (US); Lindsay Wieczorek, Chaska, MN (US)

(73) Assignee: Syngap Research Fund, San Diego, CA (US)

( * ) Notice: Subject to any disclaimer, the term of this patent is extended or adjusted under 35 U.S.C. 154(b) by 0 days.

(21) Appl. No.: 19/069,899

(22) Filed: Mar. 4, 2025

Related U.S. Application Data

(60) Provisional application No. 63/561,949, filed on Mar. 6, 2024.

(51) Int. Cl.
*A61K 31/135* (2006.01)
*A61K 31/198* (2006.01)
*A61P 25/00* (2006.01)

(52) U.S. Cl.
CPC .......... *A61K 31/135* (2013.01); *A61K 31/198* (2013.01); *A61P 25/00* (2018.01)

(58) Field of Classification Search
CPC .................................................. A61K 31/135
See application file for complete search history.

(56) References Cited

U.S. PATENT DOCUMENTS

2019/0022101 A1* 1/2019 Kujawa ................ A61K 31/166

OTHER PUBLICATIONS

Zhu, C., Lu, Y., Wang, S. et al. Nortriptyline hydrochloride, a potential candidate for drug repurposing, inhibits gastric cancer by inducing oxidative stress by triggering the Keap1-Nrf2 pathway. Sci Rep 14, 6050 (2024). https://doi.org/10.1038/s41598-024-56431-5.
Sindrup, Søren H., Troels S. Jensen, Efficacy of pharmacological treatments of neuropathic pain: an update and effect related to mechanism of drug action, Pain®, vol. 83, Issue 3,1999, pp. 389-400, ISSN 0304-3959,https://doi.org/10.1016/S0304-3959(99)00154-2.
Vlaskamp, Danique R.M. SYNGAP1 encephalopathy: A distinctive generalized developmental and epileptic encephalopathy, Neurology®, vol. 92, No. 2, 2019, pp. e96-e107, https://doi.org/10.1212/WNL.0000000000006729.
Wiltrout K, Brimble E, Poduri A. Comprehensive phenotypes of patients with SYNGAP1-related disorder reveals high rates of epilepsy and autism. Epilepsia. May 2024;65(5):1428-1438. doi: 10.1111/epi.17913. Epub Mar. 12, 2024. PMID: 38470175.
Agarwal, M., Johnston, M.V. and Stafstrom, C.E. (2019), SYNGAP1 mutations: Clinical, genetic, and pathophysiological features. International Journal of Developmental Neuroscience, 78: 65-76. https://doi.org/10.1016/j.ijdevneu.2019.08.003.
Merwar G, Gibbons JR, Hosseini SA, et al. Nortriptyline. [Updated Jun. 5, 2023]. In: StatPearls [Internet]. Treasure Island (FL): StatPearls Publishing; Jan. 2025-. Available from: https://www.ncbi.nlm.nih.gov/books/NBK482214/.
Richelson, E. Antimuscarinic and other receptor-blocking properties of antidepressants. Mayo Clin. Proc. 58, 40-46 (1983).
Moxham Presentation. Drug Repurposing Screen in Patient Models. Nov. 30, 2023, Rarebase PBC.
Nelson, Craig J. A Review of the Efficacy of Serotonergic and Noradrenergic Reuptake Inhibitors for Treatment of Major Depression. Society of Biological Psychiatry. 1999. (46) pp. 1301-1308.
Pamelor™ label, Ref ID: 3209061. Revised Oct. 2012.

* cited by examiner

*Primary Examiner* — Yong S. Chong
(74) *Attorney, Agent, or Firm* — Davidson Kappel LLC

(57) ABSTRACT

Methods of treatment of neurodevelopmental disorders via administration of organic tricyclic compounds are described. Organic tricyclic compounds administered in the method of the invention include nortriptyline, amitriptyline and their pharmaceutically acceptable salts. Pharmaceutical compositions and dosage forms containing organic tricyclic compounds are also described.

20 Claims, 16 Drawing Sheets
(15 of 16 Drawing Sheet(s) Filed in Color)

| | Variant Type | Variant |
|---|---|---|
| FM38 | Truncation (intronic) | c.3583-9G>A (p.V1195Rfs*27) |
| FM40 | Truncation (nonsense) | c.3553A>T (p.K1185*) |
| FM41 | Missense | c.1292T>C (p.L431P) |
| FM45 | Missense | c.662A>T (p.Glu221Val) |

FM38 PT3 neurons
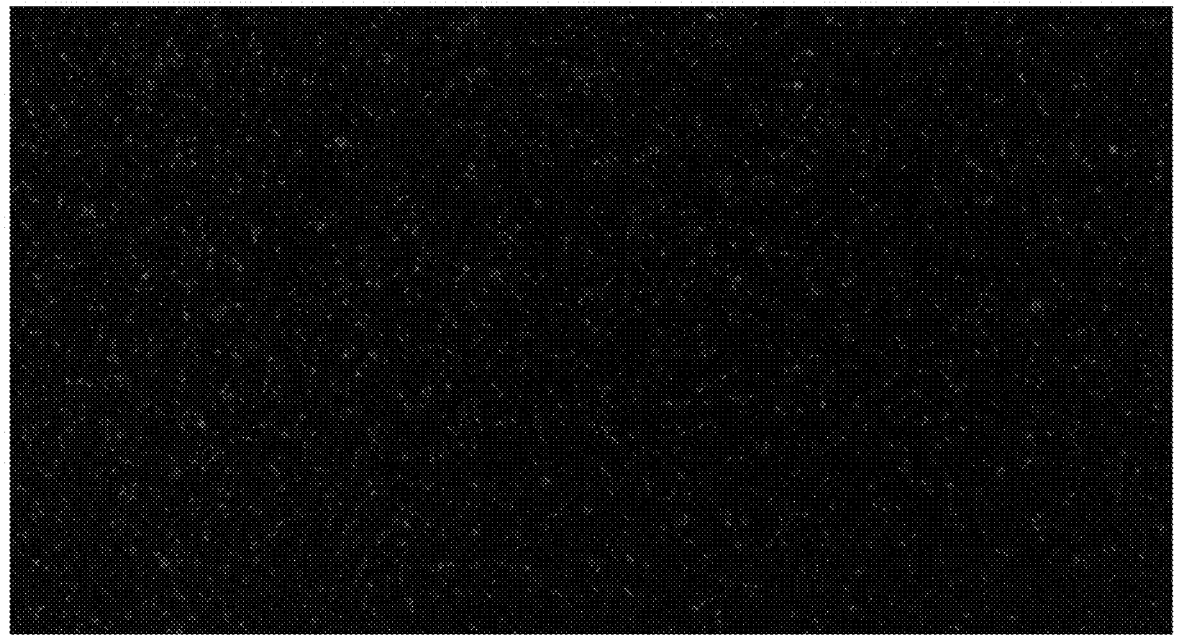
Healthy control neurons
Fig. 4

| | Pre Treatment | 5e-4 µM | 2e-3 µM | 5e-3 µM | 14e-3 µM | 4e-2 µM | 0.12 µM | 0.37 µM | 1.11 µM | 3.33 µM | 10.0 µM |
|---|---|---|---|---|---|---|---|---|---|---|---|
| REACTOME ACETYLCHOLINE NEUROTRANSMITTER RELEASE CYCLE | -1.06 | 0.84 | 0.55 | -0.61 | -0.79 | -0.41 | -1.07 | -0.86 | -1.16 | -0.92 | -0.68 |
| GOBP POSTSYNAPSE ASSEMBLY | -1.79 | 1.03 | 0.87 | 1.10 | -0.74 | -0.61 | -1.00 | 1.01 | -0.55 | -0.90 | -1.23 |
| GOBP POSTSYNAPTIC SPECIALIZATION ASSEMBLY | -1.72 | 1.43 | 1.20 | 1.29 | -0.74 | 1.37 | -0.89 | 1.28 | -0.56 | -0.67 | -1.07 |
| GOBP POSTSYNAPTIC SPECIALIZATION ORGANIZATION | -1.83 | 1.33 | 0.97 | 1.50 | -1.12 | 1.23 | -0.91 | 1.10 | -0.94 | -0.58 | -1.01 |
| GOBP REGULATION OF SYNAPSE ASSEMBLY | -1.52 | 1.12 | -0.63 | -0.79 | -1.29 | -0.62 | -1.04 | -0.68 | -1.11 | -0.96 | -1.25 |
| GOCC POSTSYNAPTIC SPECIALIZATION MEMBRANE | -2.11 | 1.50 | 1.16 | 1.27 | -1.13 | 1.62 | 1.01 | 1.23 | -0.87 | -0.78 | -1.03 |
| GOMF NEUROTRANSMITTER RECEPTOR ACTIVITY INVOLVED IN REGULATION OF POSTSYNAPTIC MEMBRANE POTENTIAL | -1.60 | 0.98 | 1.11 | 1.11 | -1.27 | -0.55 | -1.02 | -0.90 | -0.87 | -0.92 | -0.89 |

Fig. 11

METHODS FOR TREATING NEURODEVELOPMENTAL DISORDERS VIA ADMINISTRATION OF ORGANIC TRICYCLIC COMPOUNDS

CROSS REFERENCE TO RELATED APPLICATIONS

This application claims the benefit of and priority to U.S. Provisional Application No. 63/561,949, filed on Mar. 6, 2024, the entire content of which is herein incorporated by reference in its entirety.

BACKGROUND

Neurodevelopmental disorders (NDDs) are a group of conditions associated with developmental deficits that produce lifelong impairments in personal, social, academic, or occupational functioning. NDDs include, e.g., SYNGAP1-Related Disorder, SLC6A1-Related disorder, MED13L syndrome, CTNNB1 syndrome, DLG4-related synaptopathy, FOXG1 syndrome, KCNT1 epilepsy, Autism Spectrum Disorder (ASD), Intellectual Disability (ID), and other developmental and epileptic encephalopathies (DEEs). A common feature of NDDs is a decrease in synaptic plasticity and an increase in neuronal excitability.

Synaptopathies are diseases that involve dysfunctions of synapses, which are the connections between neurons in the brain, spinal cord, and peripheral nervous system. Synaptopathies include, e.g., SYNGAP1-Related Disorder, DLG4-related synaptopathy, STXBP1-disorders, Phelan-McDermid Syndrome, and Tuberous Sclerosis Complex.

SYNGAP1-Related Disorder is a rare genetic disorder caused by a pathogenic mutation in or a disruption of the SYNGAP1 gene. The SYNGAP1 gene is located on Chromosome 6 and encodes for a synaptic Ras-GTPase activating protein ("the SynGAP protein"). The SynGAP protein is highly expressed in excitatory neurons and is required for synaptic development and function. The pathogenic mutation in or the disruption of the SYNGAP1 gene leads to the gene not producing enough SynGAP protein and/or producing a disrupted SynGAP protein.

Without the proper amount and function of SynGAP protein, an increase in excitability in the synapses occurs, making it difficult for neurons to communicate effectively and leading to neurological issues seen in SYNGAP1 individuals. In addition, without the proper amount and function of SynGAP protein, a loss of synaptic plasticity also occurs. Symptoms of SYNGAP1-Related Disorder vary widely but generally include behavior disorders, sleep disturbances, epilepsy involving multiple seizure types, intellectual disability, developmental delays, autistic features or autism spectrum disorder, and gastrointestinal (GI) tract issues. SynGAP protein is also found in cilia in many cell types. Aberrant cilia formation or function may also lead to and/or intensify neurologic and other issues in individuals with SYNGAP1-Related Disorder.

SYNGAP1 variants are surprisingly common, with the incidence reported as 6 per 100,000 or 1 per 16,000 individuals.

The most common therapies available for individuals with SYNGAP1-Related Disorder are physical therapy, occupational therapy, speech therapy, developmental therapy and applied behavioral analysis (ABA) therapy. Other available therapies include antiepileptic, sleep, behavioral, and anxiety medications. For a percentage of those affected, feeding tubes and other surgeries or procedures are also standard.

While intense therapy can help SYNGAP1 patients improve their skills and reach milestones to a certain extent, there is currently no cure or specific treatment for the underlying condition that causes SYNGAP1-Related Disorder, and many symptoms of this disorder can become treatment—or drug-resistant.

DLG4-related synaptopathy (sometimes called SHINE Syndrome), is a neurodevelopmental disorder characterized by global developmental delay/intellectual disability of varying severity, autism spectrum disorder, hypotonia (loss of muscle tone) and epilepsy.

Nortriptyline is a tricyclic compound with a dibenzocycloheptene core. Nortriptyline is a prodrug of amitriptyline, which is also a tricyclic compound with a dibenzocycloheptene core. Nortriptyline is a drug often administered as nortriptyline hydrochloride and is indicated by US FDA for use in the treatment of depression in adults. A typical adult dose for the treatment of depression is 25 mg three or four times daily.

While nortriptyline presently is not US FDA approved for use in children, in some cases, it has been used in children. Known off-label uses of nortriptyline include chronic pain, anxiety disorders, diabetic neuropathy, myofascial pain, orofacial pain, migraines, and postherpetic neuralgia. Nortriptyline has also been used with patients to aid in quitting smoking and treatment of symptoms of Attention Deficit Disorder (ADD). In addition, nortriptyline is being explored for treatment of gastric cancer, tinnitus, Meniere's disease, and treatment-resistant depression.

To date, nortriptyline has usually been taken orally as a capsule or an oral solution. Capsule form comes in 10 mg, 25 mg, 50 mg, and 75 mg strengths. Oral solution forms of nortriptyline are available at a concentration of 10 mg/5 ml.

Common side effects of nortriptyline include drowsiness and sedation, which are primarily due to its antihistamine properties; dizziness and headaches, which are attributed to its anticholinergic effects; dry mouth, constipation, urinary retention, and blurred vision, which are due to nortriptyline's antagonism of muscarinic receptors, which inhibit the parasympathetic nervous system. Nortriptyline can also cause orthostatic hypotension, resulting from its blockade of alpha-1 adrenergic receptors, potentially leading to a drop in blood pressure upon standing. Arrhythmias and various degrees of heart block could occur with higher doses or overdose situations when nortriptyline blood levels exceed 500 ng/ml. Gastrointestinal issues, such as nausea and vomiting, have also been reported. Additionally, weight gain and appetite changes due to nortriptyline's histaminic and serotonergic activity could also occur.

SUMMARY OF THE INVENTION

It is an object of the invention to provide treatments for neurodevelopmental disorders.

It is an additional object of the invention to provide treatments that improve communications of a subject with a neurodevelopmental disorder.

It is an additional object of the invention to provide treatments that improve behaviors of a subject with a neurodevelopmental disorder.

It is an additional object of the invention to provide treatments that improve sleep in a subject with a neurodevelopmental disorder.

It is an additional object of the invention to provide treatments that improve sensory processing in a subject with a neurodevelopmental disorder.

It is an additional object of the invention to provide treatments that reduce severity and/or frequency of aggression in a subject with a neurodevelopmental disorder.

It is an additional object of the invention to provide treatments that increased patience of a subject with a neurodevelopmental disorder.

It is an additional object of the invention to provide treatments that increased self-control of a subject with a neurodevelopmental disorder.

It is an additional object of the invention to provide treatments that prevent, minimize or reduce seizure burden in a subject with a neurodevelopmental disorder.

It is an object of the invention to provide treatments that increase rule-shifting ability in a subject with a neurodevelopmental disorder.

It is an object of the invention to provide treatments that increase social interest or mimicry in a subject with a neurodevelopmental disorder.

It is an object of the invention to provide treatments for synaptopathies.

It is an additional object of the invention to provide treatments that improve communications of a subject with a synaptopathy.

It is an additional object of the invention to provide treatments that improve behaviors of a subject with a synaptopathy.

It is an additional object of the invention to provide treatments that improve sleep in a subject with a synaptopathy.

It is an additional object of the invention to provide treatments that improve sensory processing in a subject with a synaptopathy.

It is an additional object of the invention to provide treatments that reduce severity and/or frequency of aggression in a subject with a synaptopathy.

It is an additional object of the invention to provide treatments that increased patience of a subject with a synaptopathy.

It is an additional object of the invention to provide treatments that increased self-control of a subject with a synaptopathy.

It is an additional object of the invention to provide treatments that prevent, minimize or reduce seizure burden in a subject with a synaptopathy.

It is an additional object of the invention to provide treatments that increase rule-shifting ability in a subject with a synaptopathy.

It is an additional object of the invention to provide treatments that increase social interest or mimicry in a subject with a synaptopathy.

It is an additional object of the invention to provide treatments for SYNGAP1-Related Disorder.

It is an additional object of the invention to provide treatments that improve communications of a subject with SYNGAP1-Related Disorder.

It is an additional object of the invention to provide treatments that improve behaviors of a subject with SYNGAP1-Related Disorder.

It is an additional object of the invention to provide treatments that improve sleep in a subject with SYNGAP1-Related Disorder.

It is an additional object of the invention to provide treatments that improve sensory processing in a subject with SYNGAP1-Related Disorder.

It is an additional object of the invention to provide treatments that reduce severity and/or frequency of aggression in a subject with SYNGAP1-Related Disorder.

It is an additional object of the invention to provide treatments that increased patience of a subject with SYNGAP1-Related Disorder.

It is an additional object of the invention to provide treatments that increased self-control of a subject with SYNGAP1-Related Disorder.

It is an additional object of the invention to provide treatments that prevent, minimize or reduce seizure burden in a subject with SYNGAP1-Related Disorder.

It is an additional object of the invention to provide treatments that increase rule-shifting ability in a subject with SYNGAP1-Related Disorder.

It is an additional object of the invention to provide treatments that increase social interest or mimicry in a subject with SYNGAP1-Related Disorder.

In accordance with these objects and others, the invention provides a method of treating a neurodevelopmental disorder in a subject in need thereof comprising administering to the subject a therapeutically effective amount of a drug capable of modulating SYNGAP1 gene expression in the subject via SYNGAP1 mRNA upregulation and/or transcriptome correction and/or phenotype recovery and thereby leading to an increase in synaptic plasticity and/or a decrease neuronal excitability and/or improved ciliary function. The increase in synaptic plasticity and/or the decrease neuronal excitability and/or improved function of cilia provided by the administration of the drugs in accordance with the methods of the present invention may improve or alleviate severity of one or more symptom(s) of a neurodevelopmental disorder in a subject in need thereof. The drug capable of modulating SYNGAP1 gene expression in the subject via SYNGAP1 mRNA upregulation and/or transcriptome correction and/or phenotype recovery in accordance with the present invention may therefore have utility in treatment of neurodevelopmental disorders. Neurodevelopmental disorders amenable to treatment in accordance with the methods of the present invention include, e.g., SYNGAP1-Related Disorder, SLC6A1-Related disorder, MED13L syndrome, CTNNB1 syndrome, DLG4-related synaptopathy, FOXG1 syndrome, KCNT1 epilepsy, Autism Spectrum Disorder (ASD), Intellectual Disability (ID), and other developmental and epileptic encephalopathies (DEEs). In certain embodiments, the administration provides an improvement in communications of the subject and/or an improvement in behavior of the subject.

In one embodiment, the invention is directed in part to a method of treating a synaptopathy in a subject in need thereof comprising administering to the subject a therapeutically effective amount of a drug capable of modulating SYNGAP1 gene expression in the subject. The modulation of the SYNGAP1 gene expression afforded by the administration of the drug in accordance with the methods of the present invention may increase the amount of functional SynGAP protein in synapses in the subject and, therefore, correct a loss of synaptic plasticity and an increased neuronal excitability in the subject and, thereby, treat one or more symptom(s) of the synaptopathy in the subject. The modulation of the SYNGAP1 gene expression afforded by the administration of the drug in accordance with the methods of the present invention may also decrease burst rate and/or burst strength and/or quantity of active neurons, and, thereby, again treat one or more symptom(s) of the synaptopathy in the subject. The synaptopathies that could be treated with the methods of the present invention include, e.g., SYNGAP1-Related Disorder, DLG4-related synaptopathy, STXBP1-disorders, Phelan-McDermid Syndrome, and Tuberous Sclerosis Complex.

The invention is also directed in part to a method of treating SYNGAP1-Related Disorder in a subject in need thereof comprising administering to the subject a therapeutically effective amount of a drug capable of modulating SYNGAP1 gene expression in the subject. The modulation of the SYNGAP1 gene expression may increase the amount of functional SynGAP protein in synapses and/or improve function of cilia containing SYNGAP1 protein expression and, and therefore, correct the underlying deficiency responsible for the symptoms of SYNGAP1-Related Disorder in the subject.

The invention is also directed in part to a method of treating DLG4-related synaptopathy in a subject in need thereof comprising administering to the subject a therapeutically effective amount of a drug capable of modulating SYNGAP1 gene expression in the subject.

The modulation of the SYNGAP1 gene expression may increase the amount of functional SynGAP protein in synapses and, thereby, treat a loss of synaptic plasticity and/or an increased neuronal excitability and/or the increase function of cilia containing SYNGAP1 protein expression in the subject and one or more symptoms associated with the loss of synaptic plasticity and/or an increased neuronal excitability in the subject.

In certain embodiments, the drug administered in the methods of the invention is a tricyclic organic compound having a dibenzocycloheptene core or a dibenzoazepine core. In some of the embodiments, the tricyclic organic compound with a dibenzocycloheptene core is selected from a group consisting of nortriptyline, amitriptyline and their pharmaceutically acceptable salts. In some of the embodiments, the tricyclic organic compound with a dibenzocycloheptene core is selected from a group consisting of nortriptyline, nortriptyline hydrochloride, amitriptyline, and amitriptyline hydrochloride. In some of the embodiments, the tricyclic organic compound with a dibenzoazepine core is selected from a group consisting of desipramine, imipramine, trimipramine, and their pharmaceutically acceptable salts.

The invention is also directed in part to a method of treating a neurodevelopmental disorder in a subject in need thereof comprising administering to the subject a therapeutically effective amount of a compound having a dibenzocycloheptene core and capable of increasing SYNGAP1 gene expression in the subject.

The invention is also directed in part to a method of treating a synaptopathy in a subject in need thereof comprising administering to the subject a therapeutically effective amount of a compound having a dibenzocycloheptene core and capable of increasing SYNGAP1 gene expression in the subject.

The invention is also directed in part to a method of treating SYNGAP1-Related Disorder in a subject in need thereof comprising administering to the subject a therapeutically effective amount of a compound having a dibenzocycloheptene core substituted and capable of increasing SYNGAP1 gene expression in the subject.

The administration of the compound having a dibenzocycloheptene core may improve behaviors and/or sleep and/or sensory processing and/or reduce severity and/or frequency of aggression and/or increase patience and/or increase self-control and/or prevent, minimize or reduce seizure burden in the subject.

The invention is directed in part a method of treating a neurodevelopmental disorder in a subject in need thereof comprising administering to the subject a therapeutically effective amount of nortriptyline or a pharmaceutically acceptable salt thereof.

The invention is directed in part a method of treating a neurodevelopmental disorder in a subject in need thereof comprising administering to the subject a therapeutically effective amount of nortriptyline hydrochloride.

The invention is directed in part to a method of treating a neurodevelopmental disorder in a subject in need thereof comprising administering to the subject a therapeutically effective amount of amitriptyline or a pharmaceutically acceptable salt thereof.

The invention is directed in part a method of treating a neurodevelopmental disorder in a subject in need thereof comprising administering to the subject a therapeutically effective amount of amitriptyline hydrochloride.

The invention is directed in part a method of treating a synaptopathy in a subject in need thereof comprising administering to the subject a therapeutically effective amount of nortriptyline or a pharmaceutically acceptable salt thereof.

The invention is directed in part a method of treating a synaptopathy in a subject in need thereof comprising administering to the subject a therapeutically effective amount of nortriptyline hydrochloride.

The invention is directed in part a method of treating a synaptopathy in a subject in need thereof comprising administering to the subject a therapeutically effective amount of amitriptyline or a pharmaceutically acceptable salt thereof.

The invention is directed in part a method of treating a synaptopathy in a subject in need thereof comprising administering to the subject a therapeutically effective amount of amitriptyline hydrochloride.

The invention is directed in part a method of treating a SYNGAP1-Related Disorder in a subject in need thereof comprising administering to the subject a therapeutically effective amount of nortriptyline or a pharmaceutically acceptable salt thereof.

The invention is directed in part a method of treating a SYNGAP1-Related Disorder in a subject in need thereof comprising administering to the subject a therapeutically effective amount of nortriptyline hydrochloride.

The invention is directed in part a method of treating a SYNGAP1-Related Disorder in a subject in need thereof comprising administering to the subject a therapeutically effective amount of amitriptyline or a pharmaceutically acceptable salt thereof.

The invention is directed in part a method of treating a SYNGAP1-Related Disorder in a subject in need thereof comprising administering to the subject a therapeutically effective amount of amitriptyline hydrochloride.

The invention is also directed in part a method of improving behaviors of a subject in need thereof comprising administering to the subject a therapeutically effective amount of a drug selected from a group consisting of nortriptyline, amitriptyline and their pharmaceutically acceptable salts.

The invention is further directed in part a method of improving sleep a subject in need thereof comprising administering to the subject a therapeutically effective amount of a drug selected from a group consisting of nortriptyline, amitriptyline and their pharmaceutically acceptable salts.

The invention is also directed in part a method of improving sensory processing a subject in need thereof comprising administering to the subject a therapeutically effective amount of a drug selected from a group consisting of nortriptyline, amitriptyline and their pharmaceutically acceptable salts.

The invention is also directed in part a method of reducing severity and/or frequency of aggression a subject in need thereof comprising administering to the subject a therapeutically effective amount of a drug selected from a group consisting of nortriptyline, amitriptyline and their pharmaceutically acceptable salts.

The invention is further directed in part a method of increasing patience a subject in need thereof comprising administering to the subject a therapeutically effective amount of a drug selected from a group consisting of nortriptyline, amitriptyline and their pharmaceutically acceptable salts.

The invention is also directed in part a method of increasing self-control a subject in need thereof comprising administering to the subject a therapeutically effective amount of a drug selected from a group consisting of nortriptyline, amitriptyline and their pharmaceutically acceptable salts.

The invention is also directed in part a method of treating seizures in a subject in need thereof comprising administering to the subject a therapeutically effective amount of a drug selected from a group consisting of nortriptyline, amitriptyline and their pharmaceutically acceptable salts.

The invention is also directed in part a method of treating reduced ability to rule-shift in a subject in need thereof comprising administering to the subject a therapeutically effective amount of a drug selected from a group consisting of nortriptyline, amitriptyline and their pharmaceutically acceptable salts.

The invention is also directed in part a method of treating reduced social ability and or mimicry in a subject in need thereof comprising administering to the subject a therapeutically effective amount of a drug selected from a group consisting of nortriptyline, amitriptyline and their pharmaceutically acceptable salts.

The invention is also directed in part a method of treating epilepsy in a subject in need thereof comprising administering to the subject a therapeutically effective amount of a drug selected from a group consisting of nortriptyline, amitriptyline and their pharmaceutically acceptable salts.

The invention is also directed in part a method of treating a neurodevelopmental disease comprising administering a therapeutically effective amount of a drug selected from a group consisting of nortriptyline, amitriptyline and their pharmaceutically acceptable salts to a subject in need thereof, wherein the subject is a carrier of a SYNGAP1 gene mutation.

The invention is also directed in part a method of treating a neurodevelopmental disease comprising administering a therapeutically effective amount of a drug selected from a group consisting of nortriptyline, amitriptyline and their pharmaceutically acceptable salts to a subject in need thereof, wherein the subject is a carrier of a MED13L gene mutation.

The invention is also directed in part a method of treating a neurodevelopmental disease comprising administering a therapeutically effective amount of a drug selected from a group consisting of nortriptyline, amitriptyline and their pharmaceutically acceptable salts to a subject in need thereof, wherein the subject is a carrier of a SHANK3 gene mutation.

The invention is also directed in part a method of treating a neurodevelopmental disease comprising administering a therapeutically effective amount of a drug selected from a group consisting of nortriptyline, amitriptyline and their pharmaceutically acceptable salts to a subject in need thereof, wherein the subject is a carrier of a TSC1 or TSC2 gene mutation.

The invention is also directed in part a method of treating a neurodevelopmental disease comprising administering a therapeutically effective amount of a drug selected from a group consisting of nortriptyline, amitriptyline and their pharmaceutically acceptable salts to a subject in need thereof, wherein the subject is a carrier of a STXBP1 gene mutation.

The invention is also directed in part a method of treating a neurodevelopmental disease comprising administering a therapeutically effective amount of a drug selected from a group consisting of nortriptyline, amitriptyline and their pharmaceutically acceptable salts to a subject in need thereof, wherein the subject is a carrier of a CTNNB1 gene mutation.

The invention is also directed in part a method of treating a neurodevelopmental disease comprising administering a therapeutically effective amount of a drug selected from a group consisting of nortriptyline, amitriptyline and their pharmaceutically acceptable salts to a subject in need thereof, wherein the subject is a carrier of a DLG4 gene mutation.

The invention is also directed in part a method of treating a neurodevelopmental disease comprising administering a therapeutically effective amount of a drug selected from a group consisting of nortriptyline, amitriptyline and their pharmaceutically acceptable salts to a subject in need thereof, wherein the subject is a carrier of a KCNT1 gene mutation.

The invention is also directed in part a method of treating a neurodevelopmental disease comprising administering a therapeutically effective amount of a drug selected from a group consisting of nortriptyline, amitriptyline and their pharmaceutically acceptable salts to a subject in need thereof, wherein the subject is a carrier of a SLC6A1 gene mutation.

The invention is also directed in part a method of treating a neurodevelopmental disease comprising administering a therapeutically effective amount of a drug selected from a group consisting of nortriptyline, amitriptyline and their pharmaceutically acceptable salts to a subject in need thereof, wherein the subject is a carrier of a FOXG1 gene mutation.

The invention is also directed in part a method of treating a synaptopathy comprising administering a therapeutically effective amount of a drug selected from a group consisting of nortriptyline, amitriptyline and their pharmaceutically acceptable salts to a subject in need thereof, wherein the subject is a carrier of a SYNGAP1 gene mutation.

The invention is also directed in part a method of treating a synaptopathy comprising administering a therapeutically effective amount of a drug selected from a group consisting of nortriptyline, amitriptyline and their pharmaceutically acceptable salts to a subject in need thereof, wherein the subject is a carrier of an STXBP1 gene mutation.

The invention is also directed in part a method of treating a synaptopathy comprising administering a therapeutically effective amount of a drug selected from a group consisting of nortriptyline, amitriptyline and their pharmaceutically acceptable salts to a subject in need thereof, wherein the subject is a carrier of a SHANK3 gene mutation.

The invention is also directed in part a method of treating a synaptopathy comprising administering a therapeutically effective amount of a drug selected from a group consisting of nortriptyline, amitriptyline and their pharmaceutically acceptable salts to a subject in need thereof, wherein the subject is a carrier of a TSC1 or TSC2 gene mutation.

The invention is also directed in part a method of treating a synaptopathy comprising administering a therapeutically effective amount of a drug selected from a group consisting of nortriptyline, amitriptyline and their pharmaceutically acceptable salts to a subject in need thereof, wherein the subject is a carrier of a DLG4 gene mutation.

The invention is also directed in part a method of treating a synaptopathy comprising administering a therapeutically effective amount of a drug selected from a group consisting of nortriptyline, amitriptyline and their pharmaceutically acceptable salts to a subject in need thereof, wherein the subject is a carrier of a KCNT1 gene mutation.

The invention is also directed in part a method of treating a synaptopathy comprising administering a therapeutically effective amount of a drug selected from a group consisting of nortriptyline, amitriptyline and their pharmaceutically acceptable salts to a subject in need thereof, wherein the subject is a carrier of a SLC6A1 gene mutation.

A "gene mutation" as used in any of the methods of the invention encompasses DNA variants categorized as pathogenic, likely pathogenic, a variant categorized as a variant of uncertain significance (VUS) which may be present in an individual exhibiting symptoms of a neurodevelopmental disorder.

A "subject" as used in any of the methods of the invention include, e.g., individuals that are not depressed and not in pain and children under the age of 12.

The therapeutically effective amount of nortriptyline and nortriptyline hydrochloride administered in the methods of the invention generally ranges from about 1 mg to about 150 mg/day and are such the plasma level of nortriptyline is maintained below 150 ng/ml. In some of the embodiments, the therapeutically effective amount of nortriptyline is such that the plasma level of nortriptyline is maintained below about 40 ng/ml, about 30 ng/ml or about 20 ng/ml.

Any of the methods of treatment described above may comprise administering an initial dose of nortriptyline or a pharmaceutically acceptable salt daily for about 1 to 4 weeks and then, increasing the initial dose every 1 to 4 weeks until the desired therapeutic benefit is achieved or the dose of about 150 mg/day is reached. The initial dose may be administered at once or divided into several sub-doses to be administered two, three or four times a day. The nortriptyline dose may be administered via a route selected from the group consisting of orally, parenterally, sublingually, via suppository, nasally, topically, transdermally, intravenously, subcutaneously, intraperitoneally and via implant under the skin, depending on the preference and need of the subject and/or his or her caregiver(s). Oral administration of nortriptyline or a pharmaceutically acceptable salt in a liquid or a solid dosage form is contemplated for all of the methods of treatments described herein.

Thus, any of the methods of treatment described above may comprise administering an initial dose of nortriptyline or a pharmaceutically acceptable salt thereof orally once, twice, three times a day, or four times day for about 1 to 4 weeks and then increasing the initial dose every 1 to 4 weeks until the desired therapeutic effect is achieved. In certain embodiment, the initial dose of nortriptyline or a pharmaceutically acceptable salt thereof is from about 1 mg to about 10 mg, from about 1 mg to about 8 mg or from about 1 mg to about 6 mg. In certain embodiments, the initial dose is increased by about 1 mg, about 2 mg, about 3 mg, about 5 mg, about 6 mg, about 7 mg, about 8 mg, about 9 mg, or about 10 mg every 1 to 4 week(s).

In certain embodiments, the methods of treatment described above may comprise administering a first dose of nortriptyline or a pharmaceutically acceptable salt thereof orally once, twice, three times a day, or four times day for about 1 to 4 weeks, and then administering a second dose of nortriptyline or a pharmaceutically acceptable salt thereof orally once, twice, three times a day, or four times day for about 1 to 4 weeks, wherein the second dose is higher than the first dose, the first dose is from about 1 mg to about 10 mg, and the second dose is from about 2 mg to about 20 mg.

In certain embodiments, the methods of treatment described above may comprise administering a first dose of nortriptyline or a pharmaceutically acceptable salt thereof orally once, twice, three times a day, or four times day for about 1 to 4 weeks, and then administering a second dose of nortriptyline or a pharmaceutically acceptable salt thereof orally once, twice, three times a day, or four times day for about 1 to 4 weeks, and then administering a third dose of nortriptyline or a pharmaceutically acceptable salt thereof orally once, twice, three times a day, or four times day for about 1 to 4 weeks, wherein the second dose is higher than the first dose, the third dose is higher than the second dose, the first dose is from about 1 mg to about 10 mg, the second dose is from about 2 mg to about 20 mg, and the third dose is from about 3 mg to about 30 mg.

In certain embodiments, the methods of treatment described above may comprise administering a first dose of nortriptyline or a pharmaceutically acceptable salt thereof orally once, twice, three times a day, or four times day for about 1 to 4 weeks, and then administering a second dose of nortriptyline or a pharmaceutically acceptable salt thereof orally once, twice, three times a day, or four times day for about 1 to 4 weeks, and then administering a third dose of nortriptyline or a pharmaceutically acceptable salt thereof orally once, twice, three times a day, or four times day for about 1 to 4 weeks, and then administering a fourth dose of nortriptyline or a pharmaceutically acceptable salt thereof orally once, twice, three times a day, or four times day for about 1 to 4 weeks, wherein the second dose is higher than the first dose, the third dose is higher than the second dose, the fourth dose is higher than the third dose, the first dose is from about 1 mg to about 10 mg, the second dose is from about 2 mg to about 20 mg, the third dose is from about 3 mg to about 30 mg, and the fourth dose is from about 4 mg to about 40 mg.

In certain embodiments, the methods of treatment described above may comprise administering a first dose of nortriptyline or a pharmaceutically acceptable salt thereof orally once, twice, three times a day, or four times day for about 1 to 4 weeks, and then administering a second dose of nortriptyline or a pharmaceutically acceptable salt thereof orally once, twice, three times a day, or four times day for about 1 to 4 weeks, and then administering a third dose of nortriptyline or a pharmaceutically acceptable salt thereof orally once, twice, three times a day, or four times day for about 1 to 4 weeks, and then administering a fourth dose of nortriptyline or a pharmaceutically acceptable salt thereof orally once, twice, three times a day, or four times day for about 1 to 4 weeks, and then administering a fifth dose of nortriptyline or a pharmaceutically acceptable salt thereof orally once, twice, three times a day, or four times day for about 1 to 4 weeks, wherein the second dose is higher than the first dose, the third dose is higher than the second dose, the fourth dose is higher than the third dose, the fifth dose is higher than the fourth dose, the first dose is from about 1 mg to about 10 mg, the second dose is from about 2 mg to about 20 mg, the third dose is from about 3 mg to about 30 mg, the fourth dose is from about 4 mg to about 40 mg, and the fifth dose is from about 5 mg to about 50 mg.

In certain embodiments, the methods of treatment described above may comprise administering a first dose of nortriptyline or a pharmaceutically acceptable salt thereof orally once, twice, three times a day, or four times day for about 1 to 4 weeks, and then administering a second dose of nortriptyline or a pharmaceutically acceptable salt thereof orally once, twice, three times a day, or four times day for about 1 to 4 weeks, and then administering a third dose of nortriptyline or a pharmaceutically acceptable salt thereof orally once, twice, three times a day, or four times day for about 1 to 4 weeks, and then administering a fourth dose of nortriptyline or a pharmaceutically acceptable salt thereof orally once, twice, three times a day, or four times day for about 1 to 4 weeks, and then administering a fifth dose of nortriptyline or a pharmaceutically acceptable salt thereof orally once, twice, three times a day, or four times day for about 1 to 4 weeks, and then administering a sixth dose of nortriptyline or a pharmaceutically acceptable salt thereof orally once, twice, three times a day, or four times day for about 1 to 4 weeks, wherein the second dose is higher than the first dose, the third dose is higher than the second dose, the fourth dose is higher than the third dose, the fifth dose is higher than the fourth dose, the sixth dose is higher than the fifth dose, the first dose is from about 1 mg to about 10 mg, the second dose is from about 2 mg to about 20 mg, the third dose is from about 3 mg to about 30 mg, the fourth dose is from about 4 mg to about 40 mg, the fifth dose is from about 5 mg to about 50 mg, and the sixth dose is from about 6 mg to about 60 mg.

In certain embodiments, the methods of treatment described above may comprise administering a first dose of nortriptyline or a pharmaceutically acceptable salt thereof orally once, twice, three times a day, or four times day for about 1 to 4 weeks, and then administering a second dose of nortriptyline or a pharmaceutically acceptable salt thereof orally once, twice, three times a day, or four times day for about 1 to 4 weeks, and then administering a third dose of nortriptyline or a pharmaceutically acceptable salt thereof orally once, twice, three times a day, or four times day for about 1 to 4 weeks, and then administering a fourth dose of nortriptyline or a pharmaceutically acceptable salt thereof orally once, twice, three times a day, or four times day for about 1 to 4 weeks, and then administering a fifth dose of nortriptyline or a pharmaceutically acceptable salt thereof orally once, twice, three times a day, or four times day for about 1 to 4 weeks, and then a sixth dose of nortriptyline or a pharmaceutically acceptable salt thereof orally administering once, twice, three times a day, or four times day for about 1 to 4 weeks, and then administering a seventh dose of nortriptyline or a pharmaceutically acceptable salt thereof orally once, twice, three times a day, or four times day for about 1 to 4 weeks, wherein the second dose is higher than the first dose, the third dose is higher than the second dose, the fourth dose is higher than the third dose, the fifth dose is higher than the fourth dose, the sixth dose is higher than the fifth dose, the seventh dose is higher than the sixth dose, the first dose is from about 1 mg to about 10 mg, the second dose is from about 2 mg to about 20 mg, the third dose is from about 3 mg to about 30 mg, the fourth dose is from about 4 mg to about 40 mg, the fifth dose is from about 5 mg to about 50 mg, the sixth dose is from about 6 mg to about 60 mg, and the seventh dose is from about 7 mg to about 70 mg.

In certain embodiments, the methods of treatment described above may comprise administering a first dose of nortriptyline or a pharmaceutically acceptable salt thereof orally once, twice, three times a day, or four times day for about 1 to 4 weeks, and then administering a second dose of nortriptyline or a pharmaceutically acceptable salt thereof orally once, twice, three times a day, or four times day for about 1 to 4 weeks, and then administering a third dose of nortriptyline or a pharmaceutically acceptable salt thereof orally once, twice, three times a day, or four times day for about 1 to 4 weeks, and then administering a fourth dose of nortriptyline or a pharmaceutically acceptable salt thereof orally once, twice, three times a day, or four times day for about 1 to 4 weeks, and then administering a fifth dose of nortriptyline or a pharmaceutically acceptable salt thereof orally once, twice, three times a day, or four times day for about 1 to 4 weeks, and then administering a sixth dose of nortriptyline or a pharmaceutically acceptable salt thereof orally once, twice, three times a day, or four times day for about 1 to 4 weeks, and then administering a seventh dose of nortriptyline or a pharmaceutically acceptable salt thereof orally once, twice, three times a day, or four times day for about 1 to 4 weeks, and then administering an eighth dose of nortriptyline or a pharmaceutically acceptable salt thereof orally once, twice, three times a day, or four times day for about 1 to 4 weeks, wherein the second dose is higher than the first dose, the third dose is higher than the second dose, the fourth dose is higher than the third dose, the fifth dose is higher than the fourth dose, the sixth dose is higher than the fifth dose, the seventh dose is higher than the sixth dose, the eighth dose is higher than the seventh dose, the first dose is from about 1 mg to about 10 mg, the second dose is from about 2 mg to about 20 mg, the third dose is from about 3 mg to about 30 mg, the fourth dose is from about 4 mg to about 40 mg, the fifth dose is from about 5 mg to about 50 mg, the sixth dose is from about 6 mg to about 60 mg, the seventh dose is from about 7 mg to about 70 mg, and the eighth dose is from about 8 mg to about 80 mg.

In certain embodiments, the methods of treatment described above may comprise administering a first dose of nortriptyline or a pharmaceutically acceptable salt thereof orally once, twice, three times a day, or four times day for about 1 to 4 weeks, and then administering a second dose of nortriptyline or a pharmaceutically acceptable salt thereof orally once, twice, three times a day, or four times day for about 1 to 4 weeks, and then administering a third dose of nortriptyline or a pharmaceutically acceptable salt thereof orally once, twice, three times a day, or four times day for about 1 to 4 weeks, and then administering a fourth dose of nortriptyline or a pharmaceutically acceptable salt thereof orally once, twice, three times a day, or four times day for about 1 to 4 weeks, and then administering a fifth dose of nortriptyline or a pharmaceutically acceptable salt thereof orally once, twice, three times a day, or four times day for about 1 to 4 weeks, and then administering a sixth dose of nortriptyline or a pharmaceutically acceptable salt thereof orally once, twice, three times a day, or four times day for about 1 to 4 weeks, and then administering a seventh dose of nortriptyline or a pharmaceutically acceptable salt thereof orally once, twice, three times a day, or four times day for about 1 to 4 weeks, and then administering an eighth dose of nortriptyline or a pharmaceutically acceptable salt thereof orally once, twice, three times a day, or four times day for about 1 to 4 weeks, and then administering a ninth dose of nortriptyline or a pharmaceutically acceptable salt thereof orally once, twice, three times a day, or four times day for about 1 to 4 weeks, wherein the second dose is higher than the first dose, the third dose is higher than the second dose, the fourth dose is higher than the third dose, the fifth dose is higher than the fourth dose, the sixth dose is higher than the fifth dose, the seventh dose is higher than the sixth dose, the eighth dose is higher than the seventh dose, the ninth dose is higher than the eighth dose, the first dose is from about 1 mg to about 10 mg, the second dose is from about 2 mg to about 20 mg, the third dose is from about 3 mg to about 30 mg, the fourth dose is from about 4 mg to about 40 mg, the fifth dose is from about 5 mg to about 50 mg, the sixth dose is from about 6 mg to about 60 mg, the seventh dose is from about 7 mg to about 70 mg, the eighth dose is from about 8 mg to about 80 mg, and the ninth dose is from about 9 mg to about 90 mg.

In certain embodiments, the methods of treatment described above may comprise administering a first dose of nortriptyline or a pharmaceutically acceptable salt thereof orally once, twice, three times a day, or four times day for about 1 to 4 weeks, and then administering a second dose of nortriptyline or a pharmaceutically acceptable salt thereof orally once, twice, three times a day, or four times day for about 1 to 4 weeks, and then administering a third dose of nortriptyline or a pharmaceutically acceptable salt thereof orally once, twice, three times a day, or four times day for about 1 to 4 weeks, and then administering a fourth dose of nortriptyline or a pharmaceutically acceptable salt thereof orally once, twice, three times a day, or four times day for about 1 to 4 weeks, and then administering a fifth dose of nortriptyline or a pharmaceutically acceptable salt thereof orally once, twice, three times a day, or four times day for about 1 to 4 weeks, and then administering a sixth dose of nortriptyline or a pharmaceutically acceptable salt thereof orally once, twice, three times a day, or four times day for about 1 to 4 weeks, and then administering a seventh dose of nortriptyline or a pharmaceutically acceptable salt thereof orally once, twice, three times a day, or four times day for about 1 to 4 weeks, and then administering an eighth dose of nortriptyline or a pharmaceutically acceptable salt thereof orally once, twice, three times a day, or four times day for about 1 to 4 weeks, and then administering a ninth dose of nortriptyline or a pharmaceutically acceptable salt thereof orally once, twice, three times a day, or four times day for about 1 to 4 weeks, and then administering a tenth dose of nortriptyline or a pharmaceutically acceptable salt thereof orally once, twice, three times a day, or four times day for about 1 to 4 weeks, wherein the second dose is higher than the first dose, the third dose is higher than the second dose, the fourth dose is higher than the third dose, the fifth dose is higher than the fourth dose, the sixth dose is higher than the fifth dose, the seventh dose is higher than the sixth dose, the eighth dose is higher than the seventh dose, the ninth dose is higher than the eighth dose, the tenth dose is higher than the ninth dose, the first dose is from about 1 mg to about 10 mg, the second dose is from about 2 mg to about 20 mg, the third dose is from about 3 mg to about 30 mg, the fourth dose is from about 4 mg to about 40 mg, the fifth dose is from about 5 mg to about 50 mg, the sixth dose is from about 6 mg to about 60 mg, the seventh dose is from about 7 mg to about 70 mg, the eighth dose is from about 8 mg to about 80 mg, the ninth dose is from about 9 mg to about 90 mg, and the tenth dose is from about 10 mg to about 100 mg.

Any of the methods of treatment described above may comprise administering once, twice, three times a day, or four times day a first dose of nortriptyline or a pharmaceutically acceptable salt thereof for about 1 to 4 weeks, and then once, twice, three times a day, or four times day a second dose of nortriptyline or a pharmaceutically acceptable salt thereof for about 1 to 4 weeks, and then administering once, twice, three times a day, or four times day a third dose of nortriptyline or a pharmaceutically acceptable salt thereof for about 1 to 4 weeks, and then administering once, twice, three times a day, or four times day a fourth dose of nortriptyline or a pharmaceutically acceptable salt thereof for about 1 to 4 weeks, and then administering once, twice, three times a day, or four times day a fifth dose of nortriptyline or a pharmaceutically acceptable salt thereof for about 1 to 4 weeks, and then administering once, twice, three times a day, or four times day a sixth dose of nortriptyline or a pharmaceutically acceptable salt thereof for about 1 to 4 weeks, and then administering once, twice, three times a day, or four times day a seventh dose of nortriptyline or a pharmaceutically acceptable salt thereof for about 1 to 4 weeks, and then administering once, twice, three times a day, or four times day an eighth dose of nortriptyline or a pharmaceutically acceptable salt thereof for about 1 to 4 weeks, and then administering once, twice, three times a day, or four times day a ninth dose of nortriptyline or a pharmaceutically acceptable salt thereof for about 1 to 4 weeks, and then administering once, twice, three times a day, or four times day a tenth dose of nortriptyline or a pharmaceutically acceptable salt thereof for about 1 to 4 weeks, and then administering once, twice, three times a day, or four times day an eleventh dose of nortriptyline or a pharmaceutically acceptable salt thereof for about 1 to 4 weeks, wherein the second dose is higher than the first dose, the third dose is higher than the second dose, the fourth dose is higher than the third dose, the fifth dose is higher than the fourth dose, the sixth dose is higher than the fifth dose, the seventh dose is higher than the sixth dose, the eighth dose is higher than the seventh dose, the ninth dose is higher than the eighth dose, the tenth dose is higher than the ninth dose, the eleventh dose is higher than the tenth dose, the first dose is from about 1 mg to about 10 mg, the second dose is from about 2 mg to about 20 mg, the third dose is from about 3 mg to about 30 mg, the fourth dose is from about 4 mg to about 40 mg, the fifth dose is from about 5 mg to about 40 mg, the sixth dose is from about 6 mg to about 50 mg, the seventh dose is from about 7 mg to about 60 mg, the eighth dose is from about 8 mg to about 70 mg, the ninth dose is from about 9 mg to about 80 mg, the tenth dose is from about 10 mg to about 90 mg, and the eleventh dose is from about 11 mg to about 100 mg.

The therapeutically effective amount of amitriptyline and amitriptyline hydrochloride administered in the methods of the invention generally ranges from about 1 mg to about 200 mg/day and are such the plasma level of amitriptyline is maintained below 200 ng/ml. In some of the embodiments, the therapeutically effective amount of amitriptyline is such that the plasma level of nortriptyline is maintained below about 60 ng/ml, about 50 ng/ml or about 40 ng/ml.

Any of the methods of treatment described above may comprise administering an initial dose of amitriptyline or a pharmaceutically acceptable salt daily for about 1 to 4 weeks and then, increasing the initial dose every 1 to 4 weeks until the desired therapeutic benefit is achieved or the dose of about 150 mg/day is reached, e.g., using the regiments outlined above for nortriptyline.

The invention is also directed in part to a method of treating a neurodevelopmental disorder in a subject in need thereof comprising administering to the subject a therapeutically effective amount of a compound having a dibenzoazepine core.

The invention is also directed in part to a method of treating a synaptopathy in a subject in need thereof comprising administering to the subject a therapeutically effective amount of a compound having a dibenzoazepine core.

The invention is also directed in part to a method of treating SYNGAP1-Related Disorder in a subject in need thereof comprising administering to the subject a therapeutically effective amount of a compound having a dibenzoazepine core.

The compounds having a dibenzoazepine core that could be administered in the methods of the invention include desipramine, desipramine, trimipramine, and their pharmaceutically acceptable salts.

In the methods of the invention, the therapeutically effective amount of a compound having a dibenzoazepine core via a route selected from the group consisting of orally, parenterally, sublingually, via suppository, nasally, topically, transdermally, intravenously, subcutaneously, intraperitoneally and via implant under the skin, depending on the preference and need of the subject and/or his or her caregiver(s). Oral administration of compounds having a dibenzoazepine core is contemplated for all of the methods of treatments described herein.

In the methods of the invention, compounds having a dibenzoazepine core can be administered once-a-day, twice-a-day, three times a day, or four times a day.

In certain embodiments, the methods of the invention encompass administration of compounds having a dibenzoazepine core to individuals that are not depressed and not in pain and to children under the age of 12.

In certain embodiments, the methods of the invention further comprise administering a tricyclic organic compound having a dibenzocycloheptene core or a dibenzoazepine core with one or more additional drugs. The additional drugs may be selected from a group consisting of small molecules and biologics. In some of these embodiments, the additional drugs may be selected from a group consisting of drugs affecting localized translation of RNA into protein (subcellular localization, which requires energy, tubulin dynamics, and other specialized cell cycle processes); drugs affecting glucose and energy usage; drugs affecting mitochondrial function, efficiency, inhibition, activation, balance changes, and other effects; drugs that increase, balance or regulate any process of autophagy or time in autophagy; precision medicines; drugs that decrease, regulate, or otherwise affect the expression of proinflammatory cytokines; drugs that increase, change, balance, or modulate the complex multi-region process of vestibular compensation; drugs that decrease or regulate or balance the tyrosine catabolic processes drugs; and combinations of any of the foregoing.

In certain embodiments, the additional drugs may be selected from a group consisting of antipsychotics, benzodiazepines, antihypertensives, stimulant and non-stimulant ADD medications, antiepileptic medications, estrogens, anticholinergics, antimuscarinics, antispasmodics, antacids, steroids, muscle relaxants, beta-blockers, statins, gamma aminobutyric acid (GABA) analogues, acetylcysteine, cannabinoids, laxatives, stool softeners, bulking agents, antibiotics, antifungals, antivirals, probiotics, vitamins, and nutritional supplements.

In certain embodiments, the additional drugs may be selected from a group consisting of benzodiazepines, serotonin reuptake inhibitors, antidepressants, antipsychotics, antiepileptics; amphetamines, gamma aminobutyric acid (GABA) analogues, statins, and pharmaceutically acceptable salts of any of the foregoing.

Antiepileptics that could be used in combination with the tricyclic organic compounds having a dibenzocycloheptene core or a dibenzoazepine core in the methods of the invention include, e.g., brivaracetam, carbamazepine, clonazepam, cenobamate, ethosuximide, gabapentin, phenobarbital, phenytoin, primidone, valproate, valproic acid, felbamate, brivaracetam, eslicarbazepine, ethosuximide, lamotrigine, lacosamide, levetiracetam, oxcarbazepine, perampanel, pregabalin, cannabidiol, clobazam, fenfluramine, rufinamide, stiripentol, topiramate, tiagabine, vigabatrin, zonisamide, and pharmaceutically acceptable salts of any of the foregoing. In some of the embodiments the antiepileptic is selected from a group consisting of valproate, lamotrigine, topiramate, levetiracetam, zonisamide, gabapentin, ethosuximide, and pharmaceutically acceptable salts thereof.

Antiepileptics that could be used in combination with the tricyclic organic compounds having a dibenzocycloheptene core or a dibenzoazepine core in the methods of the invention include, e.g., aripiprazole, aripiprazole, asenapine, olanzapine, paliperidone, quetiapine, risperidone, risperidone, haloperidol, and pharmaceutically acceptable salts thereof.

Antidepressants that could be used in combination with the tricyclic organic compounds having a dibenzocycloheptene core or a dibenzoazepine core in the methods of the invention include, e.g., selective serotonin reuptake inhibitors.

Benzodiazepines that could be used in combination with the tricyclic organic compounds having a dibenzocycloheptene core or a dibenzoazepine core in the methods of the invention include, e.g., clobazam, lorazepam, alprazolam, diazepam, and pharmaceutically acceptable salts thereof.

Antihypertensive that could be used in combination with the tricyclic organic compounds having a dibenzocycloheptene core or a dibenzoazepine core in the methods of the invention include, e.g., clonidine and pharmaceutically acceptable salts thereof.

Non-stimulant ADD medications that could be used in combination with the tricyclic organic compounds having a dibenzocycloheptene core or a dibenzoazepine core in the methods of the invention include, e.g., guanfacine and pharmaceutically acceptable salts thereof.

Stimulant ADD medications that could be used in combination with the tricyclic organic compounds having a dibenzocycloheptene core or a dibenzoazepine core in the methods of the invention include, e.g., lisdexamfetamine, methylphenidate, and pharmaceutically acceptable salts thereof.

Laxatives that could be used in combination with the tricyclic organic compounds having a dibenzocycloheptene core or a dibenzoazepine core in the methods of the invention include, e.g., bisacodyl, PolyEthyleneGlycol 3350, lactulose, and pharmaceutically acceptable salts thereof.

Stool softeners that could be used in combination with the tricyclic organic compounds having a dibenzocycloheptene core or a dibenzoazepine core in the methods of the invention include, e.g., docusate and pharmaceutically acceptable salts thereof.

Bulking agents that could be used in combination with the tricyclic organic compounds having a dibenzocycloheptene core or a dibenzoazepine core in the methods of the invention include, e.g., methylcellulose and *psyllium*.

Nutritional supplements that could be used in combination with the tricyclic organic compounds having a dibenzocycloheptene core or a dibenzoazepine core include, e.g., melatonin and pharmaceutically acceptable salts thereof.

Muscarinic agents that could be used in combination with the tricyclic organic compounds having a dibenzocycloheptene core or a dibenzoazepine core in the methods of the invention include, e.g., tridihexethyl chloride.

Gamma aminobutyric acid (GABA) analogues that could be used in combination with the tricyclic organic compounds having a dibenzocycloheptene core or a dibenzoazepine core in the methods of the invention include, e.g., alfadolone, gabapentin, and pharmaceutically acceptable salts thereof.

Statins that could be used in combination with the tricyclic organic compounds having a dibenzocycloheptene core or a dibenzoazepine core in the methods of the invention include, e.g., atorvastatin, rosuvastatin, simvastatin, pravastatin, lovastatin, fluvastatin, and pharmaceutical salts thereof.

In certain embodiments, the additional drug is selected from a group consisting of onfi, valproate, lamortagine, melatonin, butyrate, risperidone, sertraline, polyethylene glycol 3350, CBD, guanfacine, trazadone, clonidine, gabapentin, levitracetam, epidialex, bisacodyl, citalopram, clonazepam, MCT/C8 oil, methylphenidate, memantine, quetiapine, epidyolex, brivaracetam, midazolam, zonisade, and pharmaceutically acceptable salts thereof.

In certain embodiments, the additional drug that could be administered in the methods of the invention with the tricyclic organic compounds having a dibenzocycloheptene core or a dibenzoazepine core include N-acetyl-L-leucine, N-acetyl-D-leucine, and N-acetyl-DL-leucine. In certain embodiment, N-acetyl-L-leucine, N-acetyl-D-leucine, and N-acetyl-DL-leucine are administered in the amounts described in U.S. application Ser. No. 19/042,105, COMPOSITIONS AND METHODS FOR TREATING NEURODEVELOPMENTAL DISORDERS, filed on Jan. 31, 2025, herein incorporated by reference.

In certain embodiments, the methods of the invention comprise administering an amount of nortriptyline or a pharmaceutically acceptable salt thereof together with an amount of N-acetyl-L-leucine. The amount of N-acetyl-L-leucine administered per day in the methods of the invention may range, e.g., from about 100 mg to about 5 grams, and may be administered orally, parenterally, sublingually, via suppository, nasally, topically, transdermally, intravenously, subcutaneously, intraperitoneally, or via an implant under the skin. In some of these embodiments, N-acetyl-L-leucine is administered orally once-a-day, two times a day, three times a day, or four times a day, as described in U.S. application Ser. No. 19/042,105, COMPOSITIONS AND METHODS FOR TREATING NEURODEVELOPMENTAL DISORDERS, filed on Jan. 31, 2025, herein incorporated by reference.

In the methods of the invention, the additional drug(s) agent, including, e.g., N-acetyl-L-leucine, may be administered in the same or different dosage form(s).

In certain embodiments, the administration of an organic compound having a dibenzocycloheptene core or a dibenzoazepine core in accordance with the methods of the invention results in an improvement in communications of the subject and/or an improvement in behaviors of the subject.

In certain embodiments, the symptom improved and/or alleviated by the administration in accordance with the methods of the invention is not seizure and is not epilepsy.

The invention is also directed in part to method for increasing the expression of SYNGAP1 gene in a subject in need thereof comprising administering a therapeutically effective amount of nortriptyline or a pharmaceutically acceptable salt thereof to the subject.

The invention is also directed in part to method for increasing the expression of SYNGAP1 gene in a subject with a neurodevelopmental disorder comprising administering a therapeutically effective amount of nortriptyline or a pharmaceutically acceptable salt thereof to the subject. In these embodiments, the neurodevelopmental disorder may be selected from a group consisting of SYNGAP1-Related Disorder, SLC6A1-Related disorder, MED13L syndrome, CTNNB1 syndrome, DLG4-related synaptopathy, FOXG1 syndrome, KCNT1 epilepsy, Autism Spectrum Disorder (ASD), Intellectual Disability (ID), and other developmental and epileptic encephalopathies.

The invention is also directed in part to method for increasing the expression of SYNGAP1 gene in a subject with a synaptopathy comprising administering a therapeutically effective amount of nortriptyline or a pharmaceutically acceptable salt thereof to the subject. In these embodiments, the synaptopathy may be selected from a group consisting of SYNGAP1-Related Disorder, DLG4-related synaptopathy, STXBP1-disorders, Phelan-McDermid Syndrome, and Tuberous Sclerosis Complex.

The invention is also directed in part to method for increasing the expression of SYNGAP1 gene in a subject with a SYNGAP1-Related Disorder comprising administering a therapeutically effective amount of nortriptyline or a pharmaceutically acceptable salt thereof to the subject.

The invention is also directed in part to the pharmaceutical compositions and dosage forms comprising a tricyclic organic compound having a dibenzocycloheptene core or a dibenzoazepine core.

Definitions

It is noted that in this disclosure and particularly in the claims and/or paragraphs, terms such as "comprises", "comprised", "comprising", and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

As used above, and throughout the specification, the following terms, unless otherwise indicated, shall be understood to have the following meanings:

The singular forms "a," "an," and "the" include plural referents unless the context clearly dictates otherwise. Thus, for example, reference to "a pathogen" includes reference to one or more of such materials and reference to "the test" refers to one or more of such processes.

The term "about" in the present specification means a value within 20% (+20%) of the value recited immediately after the term "about," including the value equal to the upper limit (i.e., +20%) and the value equal to the lower limit (i.e., −20%) of this range. For example, the phrase "about 100" encompasses any numeric value that is between 80 and 120, including 80 and 120.

The term "NTP" means nortriptyline or nortriptyline hydrochloride.

The terms "effective amount" or "therapeutically effective amount" are used interchangeably herein, and refer to an amount of a compound, formulation, material, or composition, as described herein effective to achieve a particular therapeutic result. Such results may include, but are not limited to, the treatment of a disease or condition, or one or more symptoms of a disease or condition, described herein as determined by any means suitable in the art.

The term "mutation" as used herein means a DNA variant that is classified as pathogenic, likely pathogenic or a variant of uncertain significance (VUS) with clinical features of the disease, as recognized in the art.

In the context of the present specification SYNGAP1 "pathogenic" variants include, e.g., c.333delA, c.339del, c.397_427dup31, c.410delT, c.411_418delAAAAAGCT, c.434_447dup14, c.535delG, c.557_567dup, c.654_655del, c.673delT, c.698_699dupGT, c.745del, c.768_770delCAGinsAA, c.781_784delGACA, c.828dup, c.857_864dupTGGATGAC, c.878delG, c.883_884delAC, c.883_884del, c.949delC, c.1022_1030delinsTA, c.1057_1072del, c.1127del, c.1139del, c.1142_1143insT, c.1154_1161del, c.1167_1168del, c.1167_1168delAG, c.1167delA, c.1167_1168del, c.1292del, c.1329_1333delCAAGG, c.1441_1444dup, c.1463delC, c.1685dupC, c.1744del, c.1792delC, c.1935dupT, c.2152delC, c.2152delC, c.2293delA, c.2350_2354dup, c.2354dupG, c.2438delT, c.2438delT, c.2438del, c.2516dup, c.2523_2524del, c.2561_2577del, c.2591_2592del, c.2701dup, c.2774del, c.2776_2777del, c.2843del, c.2916delT, c.2955_2958del, c.2970del, c.3167_3188dup, c.3179dup, c.3186_3199del14insAGG, c.3227delT, c.3233_3236delTCAG, c.3233_3236delTCAG, c.3233_3236del, c.3273_3274del, c.3295delT, c.3303del, c.3416dupA, c.3642delG, c.3665_3669dupGGCTG, c.1760_1792del33, c.190-15_206delins28, c.190-2A>G, c.762+1G>T, c.1676+1G>T, c.1913+2T>G, c.1913+1G>A, c.3583-6G>A, c.3583-9G>A, c.484C>T, c.812C>A, c.980T>C, c.1084T>C, c.1685C>T, c.388C>T, c.403C>T, c.427C>T, c.490C>T, c.843C>A, c.937G>T, c.1089C>A, c.1166C>A, c.1284T>A, c.1507C>T, c.1735C>T, c.1744G>T, c.1861C>T, c.2059C>T, c.2104C>T, c.2197C>T, c.2266C>T, c.2450C>G, c.2494C>T, c.2755C>T, c.2899C>T, c.2946T>A, c.3124C>T, c.3190C>T, c.3277C>T, c.3316C>T, c.3370G>T, c.3452_3453del, c.3553A>T, c.3706C>T, and c.3718C>T.

In the context of the present specification SYNGAP1 "likely pathogenic" variants include, e.g., c.333delA, c.404_411delGACGGCTAinsT, c.838dup, c.3384dup, Gain (Exon 3), c.704_707delinsTTTT, c.388-3C>G, c.1532-1G>C, c.3583-9G>A, c.3583-9G>A, c.3583-9G>A, c.3795-1G>C, c.662A>T, c.851T>C, c.968T>A, c.1030G>A, c.1292T>C, c.1394T>C, c.1403T>A, c.1706T>C, c.1714T>C, c.1797C>G, c.1802C>A, c.1847A>G, c.1889T>A, c.1898T>C, c.1946T>G, c.1958T>C, c.1988T>C, c.922C>T, c.984C>G, and c.3534C>A.

In the context of the present specification SYNGAP1 "variants of uncertain Significance" include, e.g., c.3653A>T, c.28C>T, c.250C>G, c.971G>C, c.1715C>C, c.2003C>T, c.2305C>G, c.2693C>G, c.3345_3353dupTGGGGGCAG, c.3380G>C, c.4006G>A, and Gain (Entire coding sequence).

The term "pharmaceutical composition" refers to a mixture of at least one compound of the invention with other chemical components, such as carriers, stabilizers, diluents, dispersing agents, suspending agents, thickening agents, and/or excipients. The pharmaceutical composition facilitates administration of the compound to a subject. Multiple techniques of administering a compound exist in the art including, but not limited to oral and parenteral (e.g., intravenous) administration.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability.

The term "subject" as used herein means "a human".

The term "treat" or "treating", as used herein, includes but is not limited to, alleviation or amelioration of one or more symptoms or conditions; diminishment of extent of disease, disorder, or condition; stabilized (i.e., not worsening) state of disease, disorder, or condition, or improvement in Quality of Life for the patient, family and caregivers.

The term "Quality of Life" (QOL), as used herein, refers to a measure in one or more symptoms that make a meaningful impact on the ease, comfort, happiness, or abilities of the patient, especially as they impact both the patient, the family, and the primary caregivers. Determination of QOL measures incorporates the values and the lived experience of the family, such that some symptoms, e.g. sleep or safety, may be valued above other symptoms, e.g. seizures. QOL is rated by each individual and will depend on the medical and practical specifics of each situation, along with values. The determination of changes in the Quality of Life incorporates individual choice.

The term "developmental and epileptic encephalopathies" (DEEs) describes any of at least 825 genetic disorders with neurodevelopmental and epileptic symptoms. DEEs include SYNGAP1-Related Disorder.

As used herein, "alleviate" is used interchangeably with the term "treat." Treating a disease, disorder or condition may or may not include complete eradication or elimination of the symptom.

The term "salt" means a compound that results from replacement of part or all of the acid hydrogen of an acid by a metal or a radical acting like a metal: an ionic or electrovalent crystalline compound.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such a list should be construed as a de facto equivalent of any other member of the same list solely based on their presentation in a common group without indications to the contrary.

As used herein, the term "at least one of" is intended to be synonymous with "one or more of." For example, "at least one of A, B and C" explicitly includes only A, only B, only C, or combinations of each.

The term "drug" means a compound approved by the US FDA and/or European Medicines Agency (EMA) for use in humans.

The term "improvements in behaviors" as used herein means one or more of the following: reduced incidence or severity of aggressions during therapy; elimination of aggressions during therapy; easier transitions; increased patience; increased self-control; increased interest in using the toilet; increased tolerance to task demands over any and all environments, including home and school; decreased sensitivity to environmental triggers and sensory distress; increased ability to rule switch; increased flexibility with processes and schedules; increased interest in others; increased mimicking of others; increased awareness of others and/or what another person may be experiencing; increased compliance with bedtime routines, toileting routines, and routines of daily living; increased compliance with and participation in personal self-care routines; widening of preferences and interests; increased ability to self-soothe and self-direct to appropriate activities; reduced elopement; reduced self-injury and/or desire to self-injury; reduced aggression to others, including caregivers and bystanders; decreased displays of distress, including sounds, postures, and behaviors that correlate with internal physical or psychological distress.

The term "improvements in communications" as used herein means one or more of the following: appropriate emotional expression; improvements in awareness; improvements in depth of discussion; improved eye contact; decreased frustration with receptive and expressive communication deficits; increased ability to display mild levels of concern and discomfort; increased ability to use any one or multiple modes of expressive communication including eye contact, posture and eye gaze, pointing, gesturing including sign language and modified sign language, vocalizations including words, word approximations and sounds, augmentative communication device usage including sharing, increased speed, broadening of usage, and need for more complex programming. Increases in communication may also include desire to discuss something new rather than simply asking for an object; sharing abstract feelings or thoughts rather than requests or rejections; broadening scope of interests communicated, and broadening the audience. Includes an increase in duration of conversations, even without broadening the scope. Increases in communication also encompasses increased satisfaction in communication, with or without an increase in duration or increase in scope.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 includes a chart that shows the variant types and specific SYNGAP1 variants for FM38, FM40, FM41, and FM45 iPSCs. All four cell lines are derived from peripheral blood cells from SYNGAP1-related disorder patients, and as such are heterozygous at the SYNGAP1 gene, meaning only one copy is the pathogenic variant and the other copy is unaffected (wild type).

FIG. 4 shows the Calcium imaging of SYNGAP1 FM38 PT3 neurons and healthy control neurons of Example 3. Representative calcium imaging snapshots show fluorescent calcium signals in FM38 PT3 neurons (top) and healthy control neurons (bottom). FM38 PT3 neurons display a higher density of active calcium signals, indicated by increased fluorescence, suggesting heightened network activity compared to healthy control neurons, which show fewer and more dispersed active calcium signals.

FIG. 11 is a table showing normalized enrichment scores of each pathway shown in FIG. 9 at each tested concentration of nortriptyline HCl in patient cells compared to wild-type neurons. The first column shows pre-treatment values in wild type neurons compared to patients. The pre-treatment activity level represents baseline activity for this assay. Higher nortriptyline HCl concentrations normalized hyperactive pathways in patient neurons.

FIG. 14A summarizes assessment based on Nisonger Child Behavior Rating of Example 7.

FIG. 14B summarizes assessment based on NICHQ Vanderbilt Assessment Scale, which assessed a combination of academic and relational skills, of Example 7. For this category, a high score indicates problematic performance, and a low score indicates excellent performance. Performance ratings improved over the 3 months of NTP use. Prior to starting NTP, relationships with parents, siblings and peers, overall school performance and participation in organized activities were rated as Problematic (high score). After 3 months on NTP, those same performance categories were rated as Average, demonstrating an improvement in these areas (lower score). Due to the skills (e.g. math and reading) included in the performance rating, this score was not included in the relative positive behavior ratings (FIG. 14C).

FIG. 14C shows the summary of evaluation of relative changes in overall behaviors of Example 7. An overall increase in positive behaviors was observed, including an increase in compliant and calm demeanor. A decrease in problem behaviors was also observed, most notably a reduction in inattention and conduct problems. Conduct problems encompasses a range of behaviors such as aggression, rule-breaking, defiance, and other forms of antisocial behavior. The reduction in problem behaviors was statistically significant (FIG. 14C: $p<0.0078$). Statistical analysis was performed using Wilcoxon matched-pairs signed rank test; *=$p<0.05$.

Figure 1:
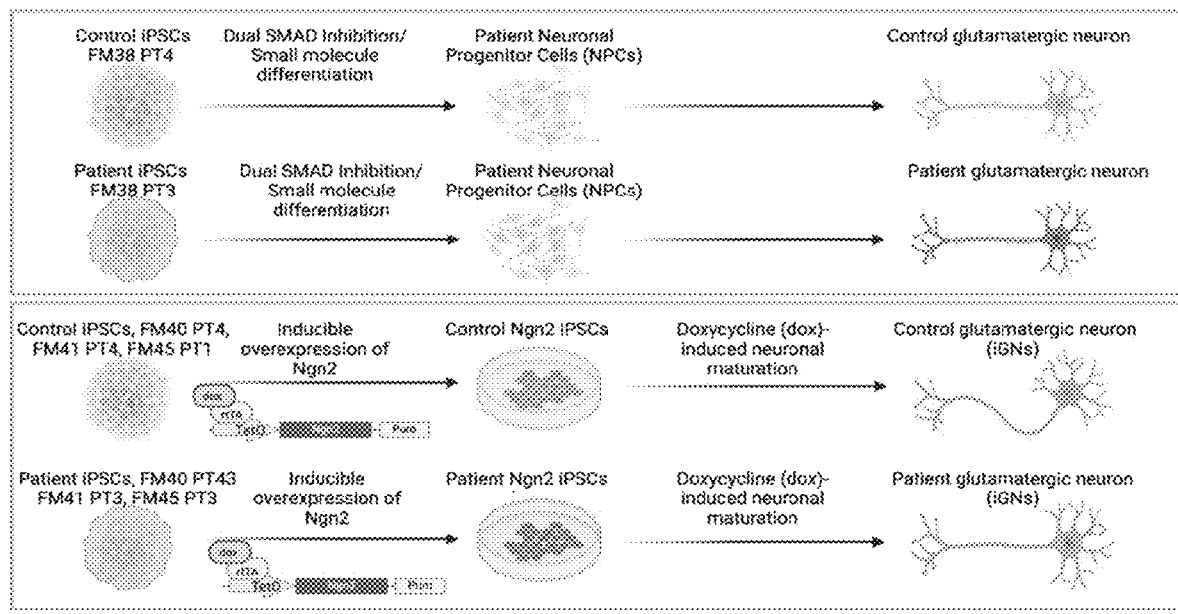
FIG. 1 shows the two pathways of differentiation of SYNGAP1 patient-derived neurons from iPSCs. Top panel: FM38 iPSCs underwent dual SMAD inhibition and small molecule differentiation, progressing through an NPC stage before maturing into glutamatergic neurons. Bottom panel: FM40, FM41, and FM45 iPSCs were engineered for doxycycline-inducible Ngn2 overexpression, allowing direct conversion into induced glutamatergic neurons (iGNs).

These drawings are provided to illustrate various aspects of the invention and are not intended to be limiting the scope in terms of dimensions, materials, configurations, arrangements or proportions unless otherwise limited by the claims.

DETAILED DESCRIPTION

Over 1,500 genes have been associated with NDDs. These genes are involved in various signaling pathways and genetic mechanisms that contribute to the development and function of the nervous system.

The genes associated with NDDs include, e.g., SYNGAP1, SLC6A1, MED13L, CTNNB1, DLG4, KCNT1, FOXG1, and genes associated with other developmental and epileptic encephalopathies. The gene function, clinical features and prevalence of some of the NDDs associated with these genes are shown in Table 1.

TABLE 1

| Gene (disorder) | Prevalence | Gene Description and Function | Clinical Features |
| --- | --- | --- | --- |
| SYNGAP1 | 1530 known 1-2 per 100,000 individuals | The SYNGAP1 gene encodes synaptic Ras GTPase-activating protein 1 (SynGAP), which is essential for normal brain function and development. SynGAP is involved in the regulation of synaptic function and plasticity. It plays a critical role in the maturation and function of dendritic spines in neurons. SynGAP1 function is crucial for learning and memory. | ASD; ID; Developmental delays in motor and language skills; Behavioral issues; Sensory processing deficits; Movement disorders and hypotonia; Seizures of various types |
| SLC6A1 | 204 known ~2.6 per 100,000 births | The SLC6A1 gene encodes the GABA transporter protein type 1 (GAT1), which is responsible for the reuptake of GABA, the primary inhibitory neurotransmitter in the brain, from the synaptic cleft back into presynaptic neurons and glia. GAT1 terminates the action of GABA by its high-affinity sodium-dependent reuptake into presynaptic terminals, thus maintaining inhibitory tone in the central nervous system. This process is crucial for regulating neuronal excitability and preventing seizures. | ASD; ID; Developmental delays; Behavioral issues; Speech and language impairment, Early onset seizures of various type |
| MED13L | ~100 known | The MED13L gene encodes for a subunit of the Mediator complex, a large complex of proteins that functions as a transcriptional coactivator for most RNA polymerase II-transcribed genes. This complex is crucial for the early development of the heart and brain. | ASD; ID; Developmental delays in motor and language skills; Distinct facial features; Congenital heart defects; Seizures |
| DLG4 | <100 known | The DLG4 gene, also known as PSD-95 or SAP-90, encodes the disc's large MAGUK scaffold protein 4, which is a postsynaptic scaffolding protein. This protein plays a critical role in synaptic plasticity, which is crucial for learning and memory. It helps organize synaptic signaling complexes at neuronal synapses, ensuring proper synaptic function and development. | ASD; ID; Developmental delays; Behavioral issues; Hypotonia, Sleep disturbances, GI difficulties; Seizures |
| CTNNB1 | ~430 known | The CTNNB1 gene encodes the beta-catenin protein, which is integral to the Wnt signaling pathway. Beta-catenin plays a critical role in cell adhesion and gene transcription regulation, and it is part of the protein complexes that form adherens junctions necessary for maintaining epithelial cell layers. | ASD; ID; Developmental delays; Behavioral issues; Speech delays and language disorders; Abnormal muscle tone; Vision impairments; Distinct facial features; Feeding difficulties and growth abnormalities |
| KCNT1 | 493 known | The KCNT1 gene encodes a sodium-activated potassium channel in brain nerve cells. Mutations in KCNT1 cause seizures and developmental delays in children. Seizures can start in infancy and be difficult to control with medication. They can include focal stiffening, shaking, or epileptic spasms. Children may not be able to walk or talk. Children may have poor muscle tone (hypotonia), dystonia, choreoathetosis, or dyskinesia. Children may also have microcephaly, autonomic instability, abnormal heart rhythms, and abnormal blood vessels in the lungs. | ID; epilepsy, motor difficulties, speech and language disorder; cardiovascular abnormalities; increased risk of early death |
| FOXG1 | ~1000 known 3.33 per individuals | The FOXG1 gene encodes the forkhead box protein G1, a transcription factor crucial for brain development. This protein regulates the activity of other genes, particularly during the development of the telencephalon, which eventually forms the cerebrum. Mutations or deletions in this gene can disrupt normal brain development, leading to significant developmental issues and structural brain abnormalities. | ASD; ID; Neurodevelopmental delays; Behavioral issues; Motor skill and visual impairments: Speech and language delays; Physical symptoms such as scoliosis, hypotonia; GI issues; Structural brain abnormalities; Seizures |

TABLE 1-continued

| Gene (disorder) | Prevalence | Gene Description and Function | Clinical Features |
|---|---|---|---|
| STXBP1 | 1,2227 patients worldwide (3 Jan. 2025 update; https://www.stxbp1disorders.org/census#:~:text = The % 2 0STXBP1 % 20census % 20is % 20a, the % 20 lives % 20of % 20STXBP1 % 20patients. | The STXBP1 gene provides instructions for making syntaxin-binding protein 1. In nerve cells (neurons), this protein helps regulate the release of chemical messengers called neurotransmitters from compartments known as synaptic vesicles. The release of neurotransmitters relays signals between neurons and is critical for normal brain function. Syntaxin-binding protein 1 may also have a role in the positioning and growth of neurons during brain development. REF: https://medlineplus.gov/genetics/gene/stxbp1/ | Seizures, Global Delays or Intellectual Disability, Speech and Communication issues, movement disorders including ataxia or tremors, feeding difficulties |
| Phelan-McDermid Syndrome (SHANK3 gene) | Estimated at 1/10,000 people or higher (difficult to diagnose) | Shank proteins are multidomain scaffold proteins of the postsynaptic density that connect neurotransmitter receptors, ion channels, and other membrane proteins to the actin cytoskeleton and G-protein-coupled signaling pathways. Shank proteins also play a role in synapse formation and dendritic spine maturation. REF: https://www.genecards.org/cgi-bin/carddisp.pl?gene = SHANK3&keywords = SHANK3 | Developmental delays, moderate to severe intellectual disabilities, speech delays, hypotonia, sleep disturbance, poor feeding, seizures, behavioral challenges, toileting challenges and chronic constipation REF: https://pmsf.org/about-pms/#whatis |
| Tuberous Sclerosis Complex (TSC) (TSC1 and TSC2 genes) | 1/6,000-10,000 people REF: https://medlineplus.gov/genetics/condition/tuberous-sclerosis-complex/#frequency | Tuberous sclerosis complex (TSC) is a multisystem disorder that results from heterozygous mutations in either TSC1 or TSC2. All Pathogenic mutations are loss of function. TSC1 and TSC2 form a complex to constitutively inhibit mechanistic target of rapamycin (mTOR) signaling cascade, and as a consequence, mTOR signaling is constitutively active within all TSC-associated lesions. | Seizures, Intellectual Disability, autism spectrum disorder, skin growth (tubers), kidney tumors and disease, heart defects and tumors, lung infections and lung disease REF: https://www.mayoclinic.org/diseases-conditions/tuberous-sclerosis/symptoms-causes/syc-20365969 |

NDDs are associated with loss of synaptic plasticity and an increased neuronal excitability.

The present inventors have found, after reviewing and testing thousands of compounds, that nortriptyline in certain human induced pluripotent stem cell (iPSC) lines has increased the gene expression of the SYNGAP1 gene.

Nortriptyline

Nortriptyline (NTP) is an organic tricyclic compound that is 3-(10,11-dihydro-5H-dibenzo[a,d]cyclohepten5-ylidene)-N-methyl. The structural formula of NTP is:

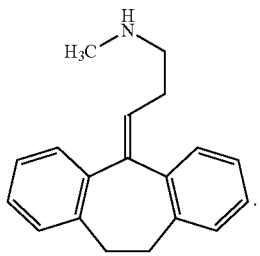 [SMILES: CNCCC=C1c2ccccc2CCc2ccccc21]

NTP is commercially available as nortriptyline hydrochloride.

NTP belongs to a class of drugs known as tricyclic antidepressants (TCA), the class of drugs that affects the levels of certain neurotransmitters in the brain. NTP was originally manufactured under the brand name Pamelor® by Merck & Co. It gained FDA approval in 1964 for treatment of major depressive disorder. It is currently widely available in generic form.

For the treatment of depression, NTP functions primarily by inhibiting the reuptake of two key neurotransmitters, serotonin and norepinephrine, at the presynaptic neuronal membrane. This inhibition prevents these neurotransmitters from being reabsorbed by the neuron that released them, thereby increasing their concentration and function in the synapse. This action is crucial for its antidepressant effects, as it helps to correct the neurotransmitter imbalances often associated with depression.

NTP also blocks the actions of other neurotransmitters, including histamine and acetylcholine, by interacting with their receptor sites. NTP use can lead to down regulation of beta-adrenergic and serotonin receptors. This down-regulation can affect the sensitivity of neuronal circuits to these neurotransmitters, contributing to its long-term effects on mood stabilization. Additionally, NTP affects cardiac ion channels, notably inhibiting sodium and calcium channels. This can explain its efficacy in treating chronic pain, such as neuropathic pain, due to its modulation of ion channel activity and neurotransmitter levels. This broad-spectrum inhibition contributes to NTPs therapeutic effects, as well as its side effect profile.

In certain embodiments of the methods of the present invention, nortriptyline may, e.g., induce expression of the SYNGAP1 gene and thereby alleviate one or more symptoms of SYNGAP1-Related Disorder.

The dose of nortriptyline used in the methods of the invention is individualized but generally ranges from about 1 mg to about 150 mg per day. In some of the embodiments, the daily dose of nortriptyline administered in the methods of the invention is from about 1 mg to about 100 mg, from about 2 mg to about 80 mg, from about 3 mg to about 60 mg, or from about 3 mg to about 40 mg. In some of the embodiments, the daily dose of nortriptyline administered in the methods of the invention is from about 1 mg to about 8 mg, from about 1 mg to about 6 mg, or from about 1 mg to about 5 mg.

In certain embodiments, the dose of nortriptyline is individualized such that the administration provides a plasma level of nortriptyline from about 5 ng/ml to about 40 ng/ml, from about 5 ng/ml to about 30 ng/ml or from about 5 ng/ml to about 25 ng/ml.

Amitriptyline

Amitriptyline is a prodrug of nortriptyline. It is an organic tricyclic compound that is 1-propanamine, 3-(10,11-dihydro-5H-dibenzo[a,d]-cyclohepten-5ylidene)-N,N-dimethyl. The structural formula of amitriptyline is:

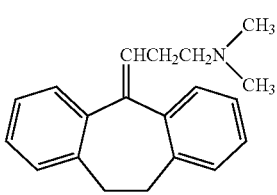

In the body, amitriptyline is metabolized to nortriptyline via removal of one methyl attached to the nitrogen.

Amitriptyline tends to have more sedative effects than nortriptyline.

Amitriptyline is commercially available as amitriptyline hydrochloride.

The dose of amitriptyline used in the methods of the invention is individualized but generally ranges from about 1 mg to about 300 mg per day. In some of the embodiments, the daily dose of amitriptyline administered in the methods of the invention is from about 1 mg to about 120 mg, from about 2 mg to about 100 mg, from about 3 mg to about 70 mg, or from about 3 mg to about 50 mg. In some of the embodiments, the daily dose of amitriptyline administered in the methods of the invention is from about 1 mg to about 10 mg, from about 1 mg to about 8 mg, or from about 1 mg to about 6 mg.

In certain embodiments, the dose of amitriptyline is individualized such that the administration provides a plasma level of amitriptyline from about 5 ng/ml to about 60 ng/ml, from about 5 ng/ml to about 40 ng/ml or from about 5 ng/ml to about 30 ng/ml.

Desipramine

Desipramine is an organic tricyclic compound that is 3-(10,11-dihydro-5H-dibenzo[b,f]azepin-5-yl)-N-methyl-propan-1-amine. The chemical formula of desipramine is:

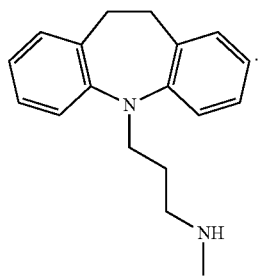 [SMILES: CNCCCN1c2ccccc2CCc2ccccc21]

The dose of desipramine used in the methods of the invention is individualized but generally ranges from about 1 mg to about 300 mg per day. In some of the embodiments, the daily dose of desipramine administered in the methods of the invention is from about 1 mg to about 250 mg, from about 2 mg to about 200 mg, from about 3 mg to about 150 mg, or from about 3 mg to about 100 mg. In some of the embodiments, the daily dose of desipramine administered in the methods of the invention is from about 1 mg to about 40 mg, from about 1 mg to about 30 mg, or from about 1 mg to about 20 mg.

In certain embodiments, the dose of desipramine is individualized such that the administration provides a plasma level of desipramine from about 5 ng/ml to about 80 ng/ml, from about 5 ng/ml to about 60 ng/ml or from about 5 ng/ml to about 40 ng/ml.

Imipramine

Imipramine is an organic tricyclic compound that is 3-(5,6-dihydrobenzo[b][1]benzazepin-11-yl)-N,N-dimethylpropan-1-amine. The chemical formula of imipramine is:

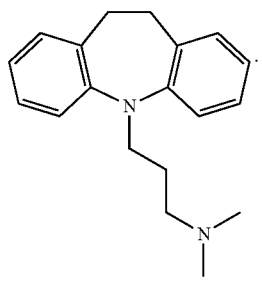 [SMILES: CN(C)CCCN1c2ccccc2CCc2ccccc21]

The dose of imipramine used in the methods of the invention is individualized but generally ranges from about 1 mg to about 300 mg per day. In some of the embodiments, the daily dose of imipramine administered in the methods of the invention is from about 1 mg to about 250 mg, from about 2 mg to about 200 mg, from about 3 mg to about 150 mg, or from about 3 mg to about 100 mg. In some of the embodiments, the daily dose of imipramine administered in the methods of the invention is from about 1 mg to about 40 mg, from about 1 mg to about 30 mg, or from about 1 mg to about 20 mg.

In certain embodiments, the dose of imipramine is individualized such that the administration provides a plasma level of imipramine from about 5 ng/ml to about 120 ng/ml, from about 5 ng/ml to about 100 ng/ml or from about 5 ng/ml to about 80 ng/ml.

Trimipramine

Trimipramine is a tricyclic compound that is 3-(10,11-dihydro-5H-dibenzo[b,f]azepin-5-yl)-N,N,2-trimethylpropan-1-amine. The chemical formula of trimipramine is:

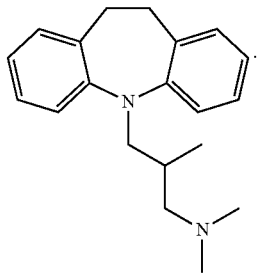 [SMILES: CC(CN(C)C)CN1c2ccccc2CCc2ccccc21]

The dose trimipramine used in the methods of the invention is individualized but generally ranges from about 1 mg to about 300 mg per day. In some of the embodiments, the daily dose of trimipramine administered in the methods of the invention is from about 1 mg to about 250 mg, from about 2 mg to about 200 mg, from about 3 mg to about 150 mg, or from about 3 mg to about 100 mg. In some of the embodiments, the daily dose of trimipramine administered in the methods of the invention is from about 1 mg to about 40 mg, from about 1 mg to about 30 mg, or from about 1 mg to about 20 mg.

In certain embodiments, the dose of trimipramine is individualized such that the administration provides a plasma level of trimipramine from about 5 ng/ml to about 120 ng/ml, from about 5 ng/ml to about 100 ng/ml or from about 5 ng/ml to about 80 ng/ml.

Pharmaceutical Compositions

Pharmaceutical compositions that are useful in the methods of invention may be prepared, packaged, or sold in formulations suitable for oral, parenteral, topical, buccal, or another route of administration. Other contemplated formulations include, e.g., nanoparticles and liposomal preparations, exosomal (including targeted exosomal) preparations, orally disintegrable preparations (e.g., tablets and films), and formulations that have an appearance of or could be added to candies, cookies, cereals, and snacks.

In certain embodiments, the pharmaceutical compositions are provided in the form, shape, size, and dose to be easily hidden or added to a food liked by the individual being treated (e.g., a sandwich cookie filling or a Nutella cookie).

The pharmaceutical compositions of the invention comprise or consist of a tricyclic organic compound having a dibenzocycloheptene core or a dibenzoazepine core, or a pharmaceutically acceptable salt thereof, and one or more pharmaceutically acceptable excipient(s).

A pharmaceutical composition of the invention may be prepared, packaged, or sold in bulk, as a single unit dose (e.g., a packet), or as a plurality of single unit doses of, e.g., a tricyclic organic compound having a dibenzocycloheptene core or a dibenzoazepine core, or a pharmaceutically acceptable salt thereof. As used herein, a "unit dose" is discrete amount of a tricyclic organic compound having a dibenzocycloheptene core or a dibenzoazepine core, or a pharmaceutically acceptable salt thereof (e.g., nortriptyline or nortriptyline hydrochloride). The amount of a tricyclic organic compound having a dibenzocycloheptene core or a dibenzoazepine core, or a pharmaceutically acceptable salt thereof is generally equal to the dosage of the tricyclic organic compound having a dibenzocycloheptene core or a dibenzoazepine core, or a pharmaceutically acceptable salt thereof that would be administered to a subject or a convenient fraction of such a dosage such as, for example, one-half or one-third of such a dosage.

In certain embodiments, the compositions of the invention may consist of a tricyclic organic compound having a dibenzocycloheptene core or a dibenzoazepine core, or a pharmaceutically acceptable salt thereof, and one or more pharmaceutically acceptable excipient(s). In certain embodiments, the compositions of the invention may consist of nortriptyline, or a pharmaceutically acceptable salt thereof, and one or more pharmaceutically acceptable excipient(s).

In certain embodiments, the compositions of the invention may be formulated using one or more pharmaceutically acceptable carriers. Pharmaceutically acceptable carriers that are useful, include, but are not limited to, glycerol, water, saline, ethanol, and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey), herein incorporated by reference. The carrier may be a solvent or dispersion medium containing, for example, water, ethanol, polyol (for example, glycerol, propylene glycol, and liquid polyethylene glycol, and the like), suitable mixtures thereof, and vegetable oils.

In certain embodiments, compositions of the invention may contain a tricyclic organic compound having a dibenzocycloheptene core or a dibenzoazepine core, or a pharmaceutically acceptable salt thereof, in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations containing the compositions of the invention may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, PA), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention include but are not limited to those selected from the group consisting of benzyl alcohol, sorbic acid, parabens, imidurea and combinations thereof. In one embodiment, a preservative comprises a combination of about 0.5% to 2.0% benzyl alcohol and 0.05% to 0.5% sorbic acid.

The composition may include an antioxidant and a chelating agent that inhibits the degradation of the compound. Preferred antioxidants for some compounds are BHT, BHA, alpha-tocopherol, and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions of the invention may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as *arachis*, olive, sesame, or coconut oil, fractionated vegetable oils, and mineral oils such as liquid paraffin. Liquid suspensions may further comprise one or more additional ingredients including, but not limited to, suspending agents, dispersing, or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredients in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as *arachis*, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

Controlled—or sustained-release formulations of a composition of the invention may be made using conventional technology, in addition to the disclosure set forth elsewhere herein. In some cases, the dosage forms to be used can be provided as slow or controlled release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the compositions of the invention.

Controlled release of an active ingredient can be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, nanoparticles, or microspheres or a combination thereof that facilitates the controlled-release of the active ingredient.

Routes of administration of any of the compositions of the invention include oral, nasal, rectal, parenteral, sublingual, transdermal, transmucosal (e.g., sublingual, lingual, (trans) buccal, (intra) nasal, and (trans) rectal, intrapulmonary, intraduodenal, intragastric, intrathecal, subcutaneous, intramuscular, intradermal, intra-arterial, intravenous, intrabronchial, inhalation, and topical administration.

For oral administration, particularly suitable are tablets, dragees, liquids, powders (e.g., granules), drops, solutions, suspensions, emulsions, capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more inert, non-toxic pharmaceutical excipients. Such excipients include, for example, an inert diluent such as lactose; granulating and disintegrating agents such as cornstarch; binding agents such as starch; and lubricating agents such as magnesium stearate. The oral compositions of the invention in the form of tablets or capsules prepared by conventional means with pharmaceutically acceptable excipients such as binding agents; fillers; lubricants; disintegrates; or wetting agents.

Tablets may be non-coated, or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and U.S. Pat. No. 4,265,874 to form osmotically controlled release tablets. Tablets may further comprise a sweetening agent, a flavoring agent, a coloring agent, a preservative, or some combination of these in order to provide for pharmaceutically elegant and palatable preparation. For oral administration, if desired, the tablets may be coated using suitable methods and coating materials such as OPADRY® film coating systems available from Colorcon, West Point, Pa. (e.g., OPADRY® OY Type, OYC Type, Organic Enteric OY—P Type, Aqueous Enteric OY-A Type, OY-PM Type and OPADRY® White, 32K18400).

Hard capsules comprising the active ingredients may be made using a physiologically degradable composition, such as gelatin. Such hard capsules comprise the active ingredient, and may further comprise additional ingredients including, for example, an inert solid diluent such as calcium carbonate, calcium phosphate, or kaolin. Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid preparation for oral administration may be in the form of solutions, syrups, or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters, or ethyl alcohol); and preservatives (e.g., methyl or propyl para-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface-active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, "parenteral administration" is contemplated to include, but is not limited to, intraocular, intravitreal, subcutaneous, intraperitoneal, intramuscular, intrasternal injection, intratumoral, and kidney dialytic infusion techniques. "Parenteral administration" is also contemplated to include lumbar puncture for injection into cerebrospinal fluid.

Administration in accordance with the methods of the invention also encompasses administration through a feeding tube.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen free water) prior to parenteral administration of the reconstituted composition.

A pharmaceutical composition of the invention may be prepared, packaged, or sold in a formulation suitable for oral administration.

A pharmaceutical composition of the invention may be prepared, packaged, or sold in a formulation suitable for topical administration. There are several advantages to delivering compounds, including drugs or other therapeutic agents, into the skin (dermal drug delivery) or into the body through the skin (transdermal drug delivery). Transdermal compound delivery offers an attractive alternative to injections and oral medications.

Dosage Forms

The compositions of the invention may be formulated into a pharmaceutically acceptable oral dosage form. Oral dosage forms may include but are not limited to, oral solid dosage forms and oral liquid dosage forms. Oral solid dosage forms may include but are not limited to, tablets, capsules, caplets, powders, pellets, multiparticulates, beads, spheres and/or any combinations thereof. These oral solid dosage forms may be formulated as immediate release, controlled release, sustained (extended) release or modified release formulations.

The oral solid dosage forms of the present invention may also contain pharmaceutically acceptable excipients such as fillers, diluents, lubricants, surfactants, glidants, binders, dispersing agents, suspending agents, disintegrants, viscosity-increasing agents, film-forming agents, granulation aid, flavoring agents, sweetener, coating agents, solubilizing agents, and combinations thereof as outlined in detail above. Each of these excipient(s) may, e.g., comprise from about 0.1% to about 99.9%, from about 0.5% to about 95%, from about 1% to about 95%, from about 2% to about 95%, from about 3% to about 95%, or from about 5% to about 95% of the formulation by weight.

The compositions of the invention may also be formulated into a pharmaceutically acceptable parenteral dosage form.

The compositions of the invention may also be formulated into a pharmaceutically acceptable transdermal dosage form.

Additional dosage forms of this invention include dosage forms as described in U.S. Pat. Nos. 6,340,475; 6,488,962; 6,451,808; 5,972,389; 5,582,837 and 5,007,790. Additional dosage forms of this invention also include dosage forms as described in U.S. patents applications Ser. Nos. 20/030, 147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Administration

The compounds and compositions of the present invention may be used as therapy to treat neurodevelopmental disorders, including synaptopathies. Neurodevelopmental disorders amenable to treatment by the methods of the present invention include, e.g., SYNGAP1-Related Disorder, SLC6A1-Related disorder, MED13L syndrome, CTNNB1 syndrome, DLG4-related synaptopathy, STXBP1 disorder, Phelan McDermid Syndrome, Tuberous Sclerosis Complex, KCNT1 epilepsy, and FOXG1 syndrome, Autism Spectrum Disorder (ASD), Intellectual Disability (ID), and other developmental and epileptic encephalopathies.

The compounds and compositions of the present invention may be administered by any pharmaceutically effective route. For example, the compounds and compositions of the invention can be administered in liquid, tablet, parenteral, transrectal, transdermal or in any other form of administration or formulation suitable in order to achieve a therapeutic effect. Such formulations may contain additional fillers, carriers, excipient or excipients, inert or not, as outlined above or known to those skilled in the art of pharmaceutical preparations, in order to provide appropriate dose, volume, and/or facilitate absorption of the active drug(s).

Subjects amenable to treatment include individuals showing symptoms of neurodevelopmental disorders and individuals having a mutation in SYNGAP1, SLC6A1, MED13L, CTNNB1, DLG4, STXBP1, SHANK3, TSC1, TSC2, KCNT1, or FOXG1 gene associated with clinical manifestations of a neurodevelopmental disorder but not showing symptoms. Thus, in certain embodiments, the treatment includes prophylactic administration of the compounds of the invention to an individual not exhibiting symptoms of neurodevelopmental disorders, e.g., in an effort to prevent and/or delay appearance of symptoms of a neurodevelopmental disorder in the subject or to prolong symptom-free period.

Treatment typically entails multiple dosages over a period of time. The period of time may, e.g., be from 1 week to 52 weeks, from 1 week to 26 weeks, from 2 weeks to 26 weeks, or from 3 weeks to 26 weeks. The treatment may also continue for as long as a therapeutic benefit is observed. Treatment may also be provided on an intermittent or on as needed basis.

Therapeutically effective doses of the compositions of the present invention, for the treatment of the above-described conditions may vary depending upon many different factors, including means of administration, target site, physiological state of the subject, other medications administered, but would generally range between about 1 mg to about 300 mg. In view of the information provided herein, therapeutically effective amounts or doses can be determined and optimized using standard clinical techniques by a person of ordinary skill in the art.

Example 1

Patient-derived SYNGAP1 neurons were generated using iPSC lines FM38, FM40, FM41, and FM45 as shown in FIG. 1. FM38 and FM40 carry truncated variants (c.3583-9G>A (intronic, p.V1195Rfs*27) and *c.3553A>T (p.K1185)**, respectively), while FM41 and FM45 harbor missense mutations (c.1292T>C and c.662A>T, respectively).

FM38 iPSCs underwent dual SMAD inhibition and small molecule-directed differentiation, progressing through a neuronal progenitor cell (NPC) stage before maturing into glutamatergic neurons. In contrast, FM40, FM41, and FM45 iPSCs were engineered for doxycycline-inducible overexpression of Neurogenin-2 (Ngn2), allowing for rapid and direct conversion into glutamatergic neurons without passing through an NPC stage.

Figure 2:
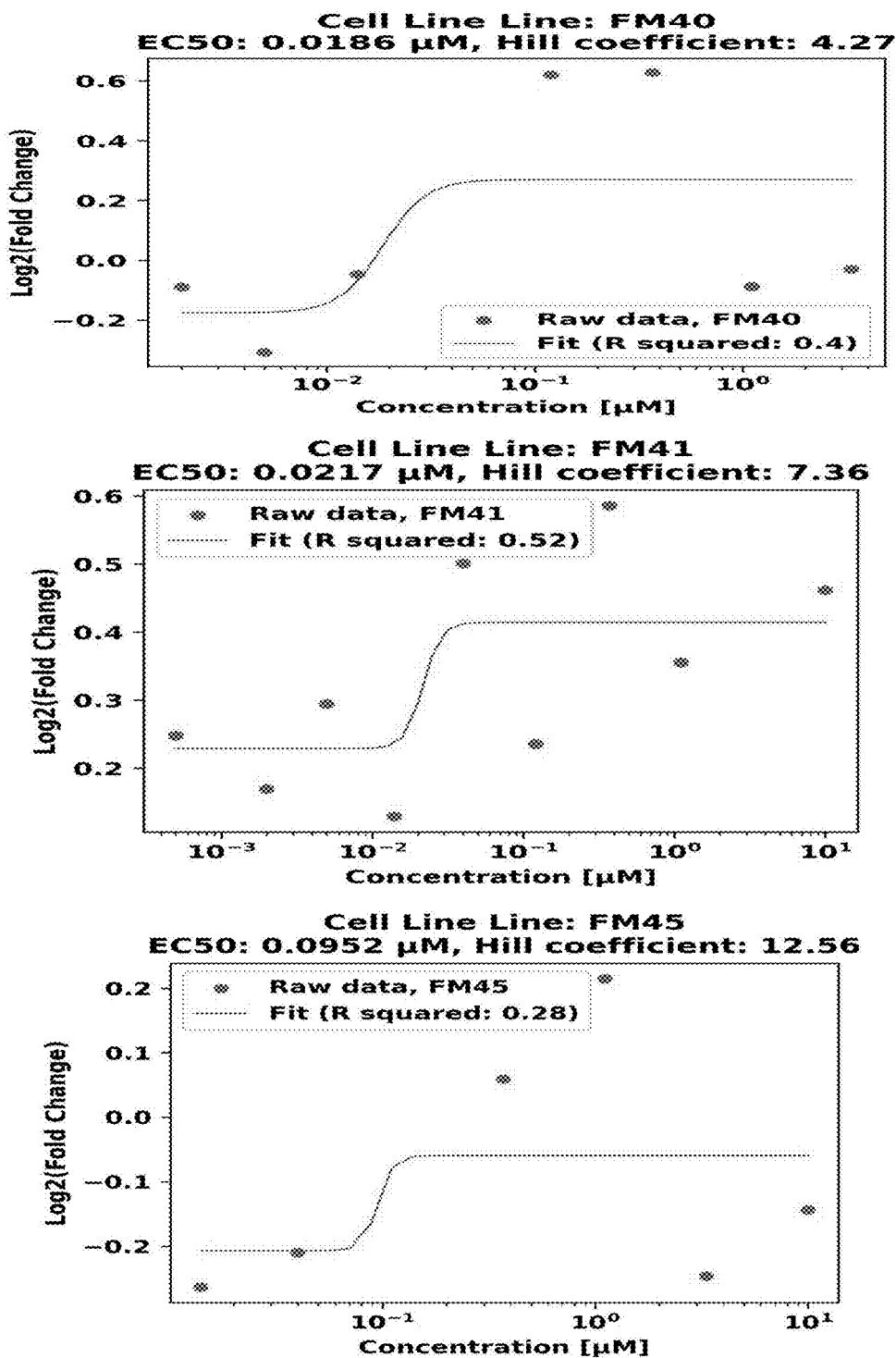
FIG. 2 shows the effect of varying concentrations of nortriptyline HCl one-fold changes for three different iPSC lines of Example 1. The data shows clear increases at certain concentrations and that, surprisingly, concentrations of nortriptyline HCl between $10^{-1}$ and 100 µM at the iPSC level may lead to optimal expression.

Effects of varying concentrations of nortriptyline on three different iPSC lines of SYNGAP1 (FM40, FM41 and FM45) in the lowly expressing SYNGAP1 wells were determined. The low-count wells are cell type dependent compared to the high-count wells. The data is summarized in FIG. 2.

It was concluded that, in FM40, up-regulation occurred at lower concentrations followed by down-regulation to basal levels, and that both FM41 and FM45 also showed an up-regulation only in the low-count wells. In FM45, SYNGAP1 was up-regulated and down-regulated to basal levels at higher nortriptyline concentrations.

It was further concluded that nortriptyline hydrochloride shows a very small effect on SYNGAP1 in the missense lines.

Example 2

Drug treatment effects of nortriptyline hydrochloride on neuronal viability of Syngap patients and control cell lines were studied. It was concluded that nortriptyline hydrochloride up-regulates SYNGAP1 in cells carrying the truncation variants (iPSC FM38 and FM40 lines). Both FM38 and FM40 showed up-regulation in SYNGAP1 in high and low count wells, respectively. In FM40, up-regulation occurred at lower concentrations followed by down-regulation to basal levels.

Figure 3:
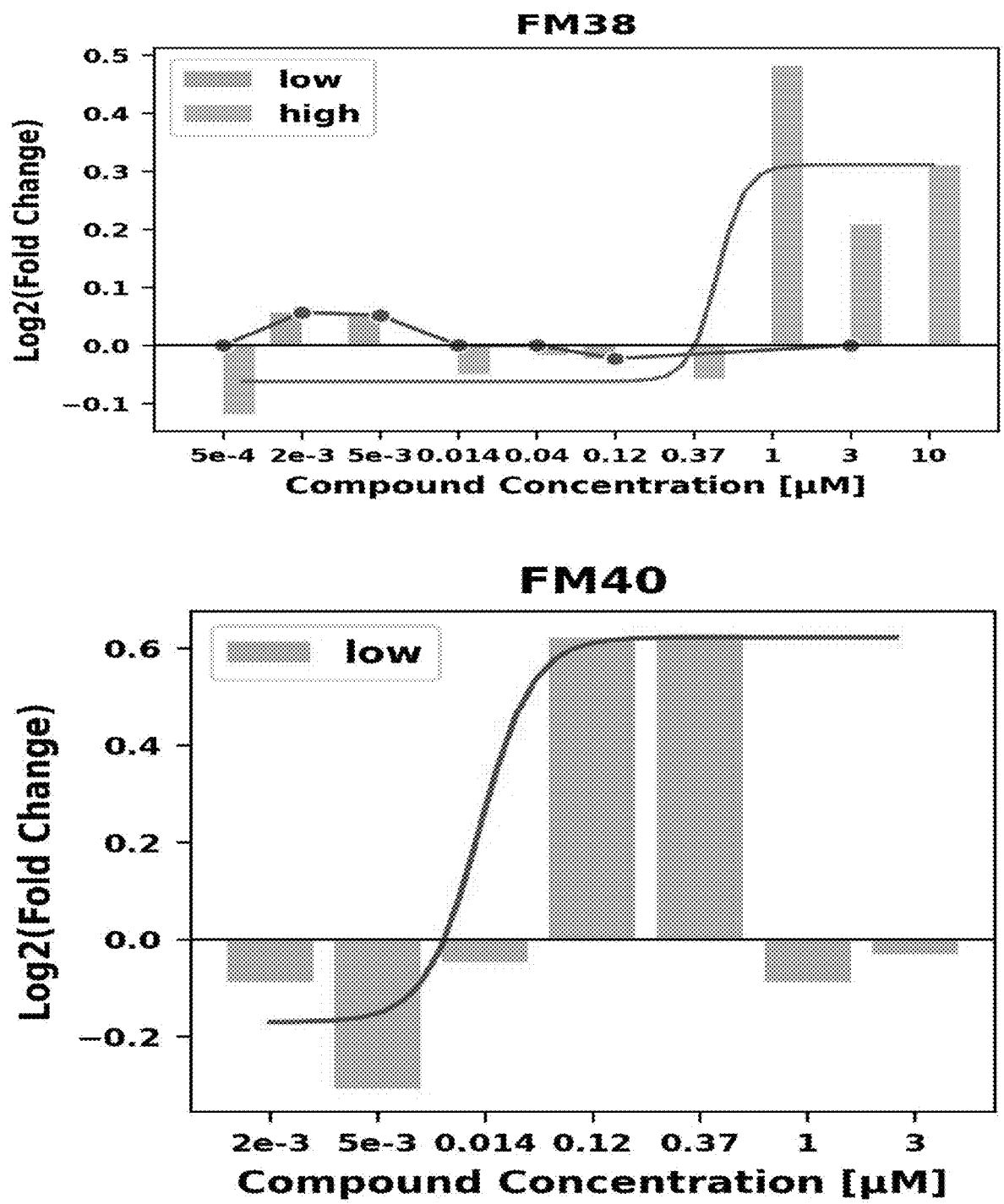
FIG. 3 shows the results of Example 2. Nortriptyline HCl up-regulates SYNGAP1 in cells carrying the truncation variants in iPSC FM38 and FM40 lines. Both FM38 and FM40 showed up-regulation in SYNGAP1 in high and low count wells, respectively. In FM40, up-regulation occurred at lower concentrations followed by down-regulation to basal levels.
Figure 5:
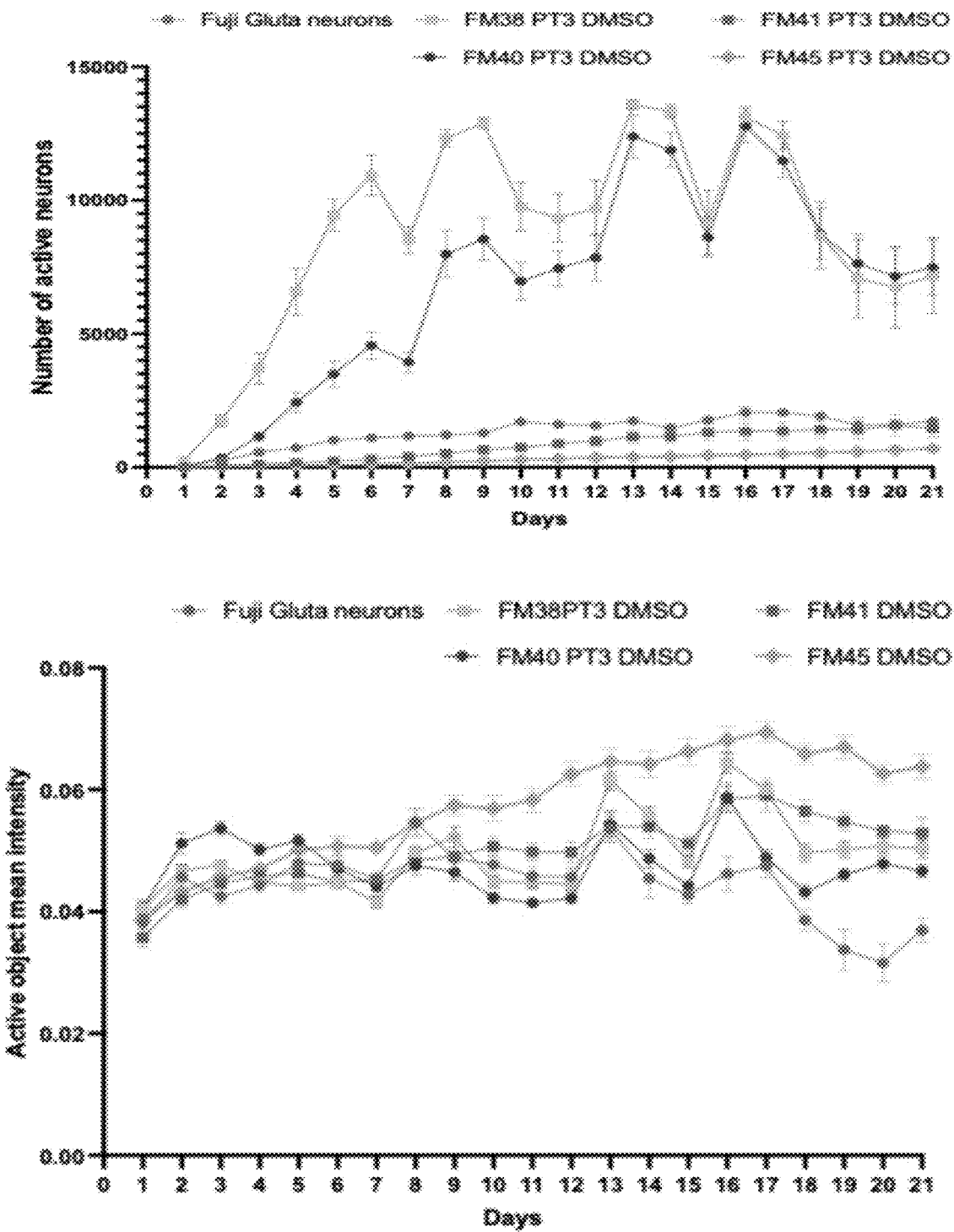
FIG. 5 shows a comparison of neuronal activity of Syngap1 patient cell lines with a healthy control cell line (Calcium Imaging of FM38 PT3 patient neurons) of Example 3. (Top panel): The number of active neurons was tracked over 21 days in patient-derived SYNGAP1 iPSC neurons (FM38, FM40, FM41, FM45) and control Fuji glutamatergic neurons. FM38 and FM40 neurons showed a higher number of active neurons compared to FM41 and FM45, which remained low throughout the experiment. Means ±Standard deviation, 2-way ANNOVA with Bonferroni's post-hoc test, DMSO vs nortriptyline treatment for FM38 and FM40, *** $p<0.001$ day 14 to 18. Bottom panel: shows the mean active object intensity, representing the strength of neuronal activity, measured over time. FM45 neurons exhibited the highest activity intensity, whereas FM38, FM40, and FM41 displayed lower and relatively stable activity levels. Control Fuji glutamatergic neurons maintained consistently low activity. Error bars indicate the standard error of the mean (SEM).
Figure 6:
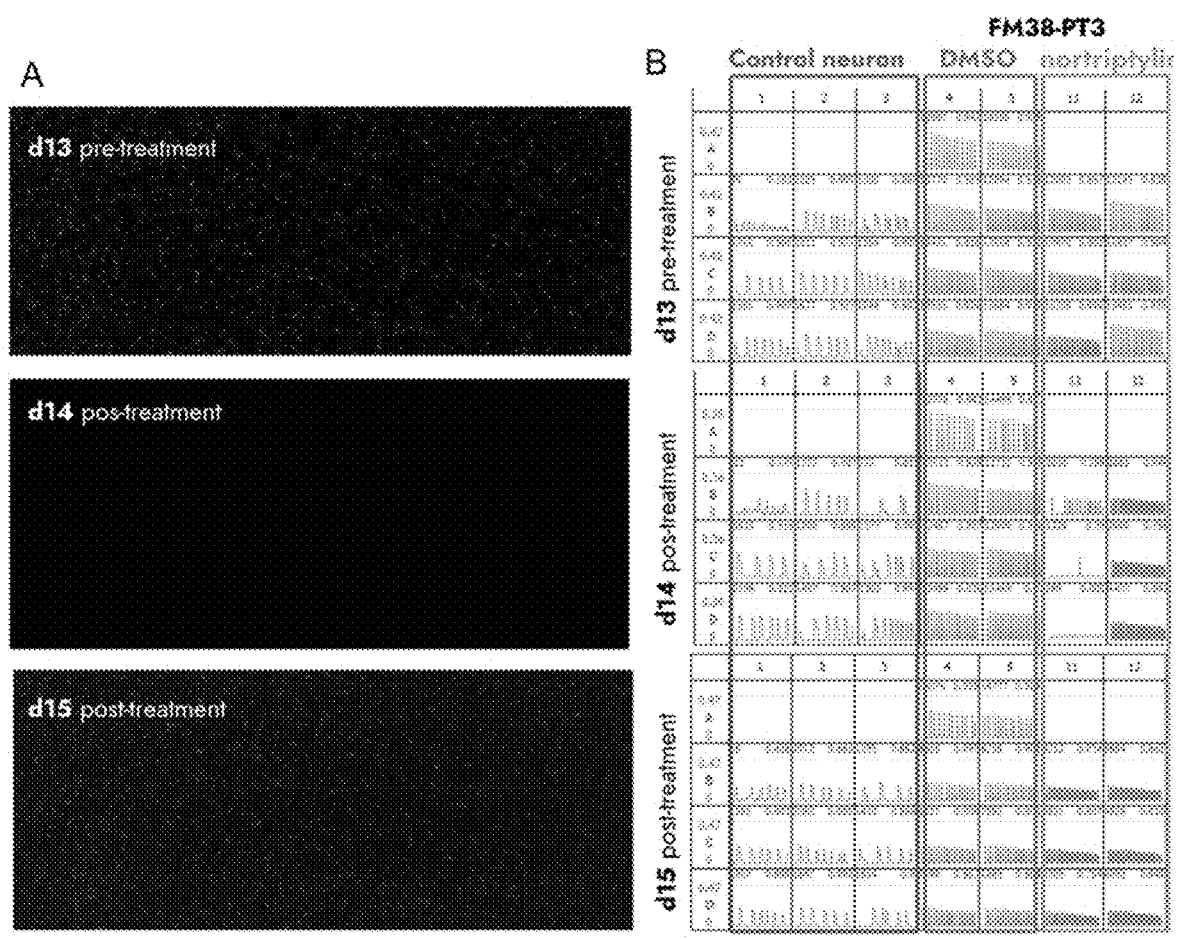
FIG. 6 shows neuronal activity decreases in FM38 patient neurons following nortriptyline HCl treatment in Example 3; nortriptyline strongly decreases neuronal network activity, with effects persisting beyond 24 hours post-treatment. A: Calcium imaging snapshots of FM38-PT3 neurons before and after nortriptyline treatment. On Day 13 (pre-treatment), neurons exhibit high levels of calcium activity, indicated by abundant fluorescent signals. On Day 14 (12 hours post-treatment), fluorescence is nearly absent, suggesting a strong suppression of neuronal activity. By Day 15 (2 days post-treatment), calcium activity partially recovers but remains lower than pre-treatment levels. B: Calcium oscillation traces summarizing neuronal activity in control neurons (red), DMSO-treated neurons (blue), and nortriptyline-treated neurons FM38 PT2 neurons (green). Pre-treatment (Day 13) shows frequent and synchronized calcium bursts in all conditions. Following nortriptyline treatment (Day 14), oscillation frequency and intensity are markedly reduced, indicating dampened neuronal excitability. By Day 15, nortriptyline-treated neurons show partial recovery, but activity remains suppressed compared to DMSO and control neurons.
Figure 7:
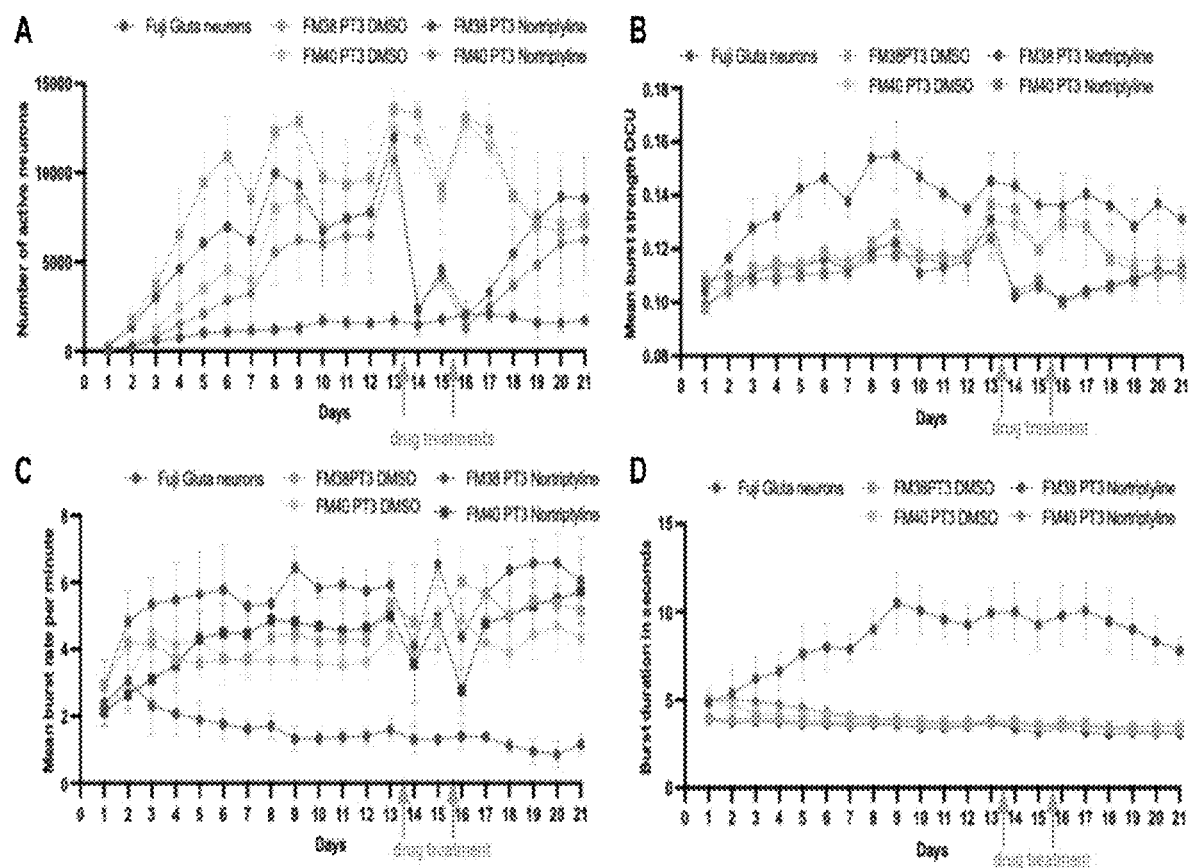
FIG. 7 shows the effects of nortriptyline on neuronal network activity in SYNGAP1 patient-derived neurons of Example 3; the burst rate, burst strength and quantity of active neurons decline for longer periods of times following nortriptyline HCl treatment. Nortriptyline dampens hyperactive network activity in SYNGAP1 patient-derived neurons, primarily by reducing the number of active neurons, burst strength, and burst frequency, while having little effect on burst duration. (A) before nortriptyline treatment, FM38 and FM40 neurons exhibit higher active neuron counts compared to Fuji control neurons. Following nortriptyline treatment (Day 13-15, indicated by blue arrows), active neuron numbers sharply decline, with partial recovery observed by Day 16-21. (B) mean burst strength; nortriptyline treatment reduces burst intensity, with FM38 and FM40 neurons displaying lower burst strength than Fuji controls. (C) mean burst rate per minute; FM38 and FM40 neurons initially exhibit higher burst frequencies, which drop significantly after nortriptyline treatment, suggesting decreased neuronal excitability. 7: burst duration remains relatively stable across conditions, with nortriptyline treatment having a minimal effect on burst duration. Means ±standard deviation, 2-way ANOVA with Turkey's post-hoc test: DMSO vs nortriptyline treatment for FM38 and FM40, * $p<0.001$ day 14 to 18 (A, B)  $p<0.01$ day 16 (C).

The results are summarized in FIG. 3.

Example 3

Neuronal activities of Syngap1 patient cell lines with a healthy control cell line were compared.

Glutamatergic control neurons (Fujifilm) and Syngap1 PT38, 40, 41 and 45 patient neurons were plated with astrocytes (Fujifilm) on 96-well plates and matured in Brainphys maturation media for 14 days. Then, Co-cultures were infected with Neuroburst Calcium Imaging Lentivirus on day 14 and assayed for calcium activity in the IncuCyte for 21 days (from day 16 to day 37 of neuronal maturation). Drug treatment occurred twice on days 30 and 32 with 2 µM nortriptyline HCl.

The results are summarized in FIGS. 3, 4, 5, and 6.

It was concluded that FM38 and FM40 patient neurons show significantly increased neuronal activity, that neuronal activity decreases in FM38 patient neurons following nortriptyline HCL treatment, and that the burst rate, burst strength and quantity of active neurons decline for longer periods of times following nortriptyline HCl treatment.

It was also concluded that nortriptyline induces cells to display a phenotype, by calcium imaging, that is moving directionally to be more similar to control neurons.

Example 4

RNA-seq results: nortriptyline HCl reverses pathway disease profile of SYNGAP1-related disorder patient cell lines.

Each of the patient lines was characterized using bulk RNA-sequencing. RNA extraction was performed using Qiagen RNeasy Plus Mini Kit (Qiagen, Cat: 74134). RNA quality and purity was checked by testing 2 µL of RNA on a High Sensitivity RNA screentape (Agilent Tapestation). RNA concentration was quantified using a Qubit 4 Fluorometer (Invitrogen). Bulk RNA libraries were prepared from 200 ng of RNA input using Illumina Stranded Total RNA Prep with Ribo-Zero Plus kit. RNA library quality was checked by running 1 uL of each library on a High Sensitivity D1000 screentape (Agilent Tapestation), and concentration was quantified by qPCR using a KAPA Universal Illumina library quantification kit (Roche). Samples were sequenced in batches of 8 or less, on a NextSeq 1000 using the standard loading protocol for a P2 200 cycle sequencing cartridge.

Libraries were prepared using a customized version of the DRUG-seq protocol (Ye et. al.). Briefly, cell culture media was aspirated using a STARlet liquid handler (Hamilton) and lysis buffer was dispensed directly into each well with a Multidrop Combi Reagent Dispenser (ThermoFisher Scientific) and placed on a shaker for 15 minutes at 900 rpm. Cell lysate was transferred into 384-well PCR plates and reverse transcription (RT) mix was dispensed into each well. Using an Echo 650 Liquid Handler (Beckman Coulter), barcoded RT primers were dispensed into each well. Plates were incubated at 42° C. for 2 hours. Following RT, each well was pooled into a single tube and purified using DNA Clean & Concentrator-100 (Zymo Research) followed by concentration with Agencourt RNAClean XP beads (Beckman Coulter). Single-stranded DNA was removed by incubating cDNA with Exonuclease I (New England Biolabs) followed by pre-amplification of the cDNA with DRUG-seq PCR primers. cDNA was fragmented and tagged with Illumina sequencing adapters using Tagmentation DNA Enzyme (TDE1). A final PCR was performed to amplify the libraries and add P7, P5, and index sequences. Libraries were sequenced on a NovaSeq 6000 (Illumina).

RNA-seq Data Analysis was conducted. RNA-seq reads were aligned using the pseudo-alignment software Kallisto (https://pachterlab.github.io/kallisto/) v 0.46.1 with bootstrapping (number of bootstraps=100) (Bray et. al.). Reads were aligned to the human GrCh38 assembly to generate transcript-level counts. Transcript counts were converted to gene counts using the human transcript to gene map version 107.

Differential expression was analyzed. For bulk RNA-sequencing, differential expression was performed at the gene-level using Kallisto's sister package Sleuth (https://pachterlab.github.io/sleuth/about.html) v0.30.0 using median-of-ratios normalization followed by shrinkage in R (Pimentel et. al.). Differential expression was performed between a control and a test group. The output yielded a gene-level log 2 (Fold Change) of the test group compared to the control group. For all comparisons the control group was the familial control sample unless mentioned otherwise.

For high-throughput screening, differential expression analysis was performed using pyDESeq2 comparing cells treated with the drug to those treated with a DMSO vehicle control.

Gene set enrichment analysis (GSEA) was performed using the fGSEA package v1.22.0 (https://bioconductor.org/packages/release/bioc/html/fgsca.html) in R based on the gene-level fold change values from two-condition DE analysis (Korotkevich et. al.). Enrichment was calculated for pathways downloaded from the Molecular Signatures Database (https://www.gsca-msigdb.org/gsca/msigdb) MSigDB. For high-throughput drug screens, concentration-response fold changes were analyzed using a concentration-aware GSEA in python.

The disease profile associated with SYNGAP1 was characterized using bulk RNA-sequencing of the patient and the corresponding familial control lines.

Figure 8:
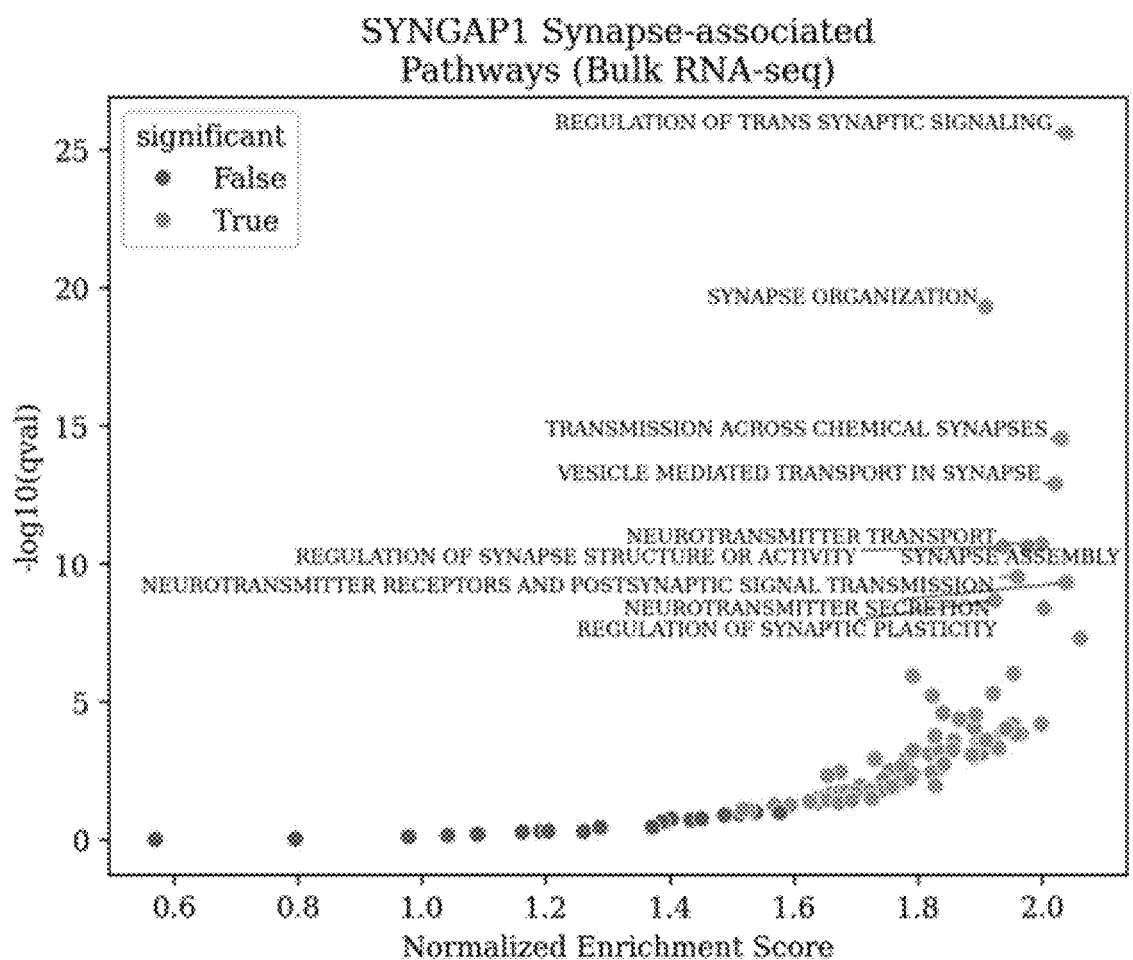
FIG. 8 is a gene set enrichment analysis of patient lines vs. control in Example 4 showing increased activity of pathways associated with synaptic plasticity and signaling, synapse organization and transmission.
Figure 9:
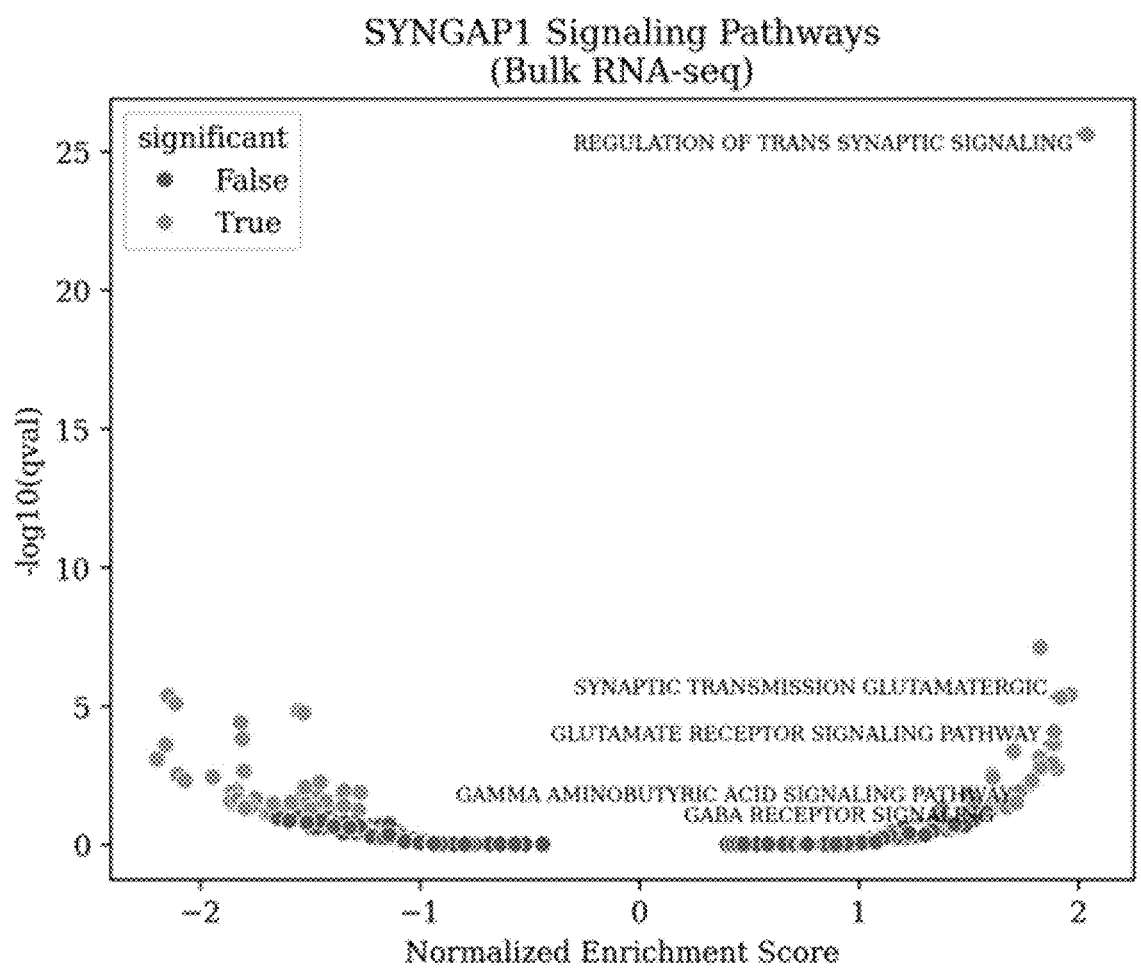
FIG. 9 depicts SYNGAP1 patient derived lines showing increased glutamatergic signaling compared to control lines in Example 4. SYNGAP1 deficiency in the patient was found to be associated with both increased synaptic potentiation and excitatory signaling via glutamate.

A comparison of the patient lines to the control lines showed that pathways involved in synapse formation and the transmission of neurotransmitters that facilitate synaptogenesis were found to be significantly enriched in the patient lines (FIG. 8) and that SYNGAP1 down-regulation is associated with higher glutamatergic signaling activity (FIG. 9). It was concluded that SYNGAP1 deficiency in the patient is associated with both increased synaptic potentiation and excitatory signaling via glutamate.

Example 5

In a high-throughput drug screen NGN2-derived excitatory neurons from patient cells were compared to wildtype excitatory neurons at various nortriptyline HCl concentrations. It was concluded that seven synaptic pathways exhibited significant (p-value <0.05) dose-dependent activity in SYNGAP1 patient lines treated with nortriptyline Hydrochloride.

Figure 10:
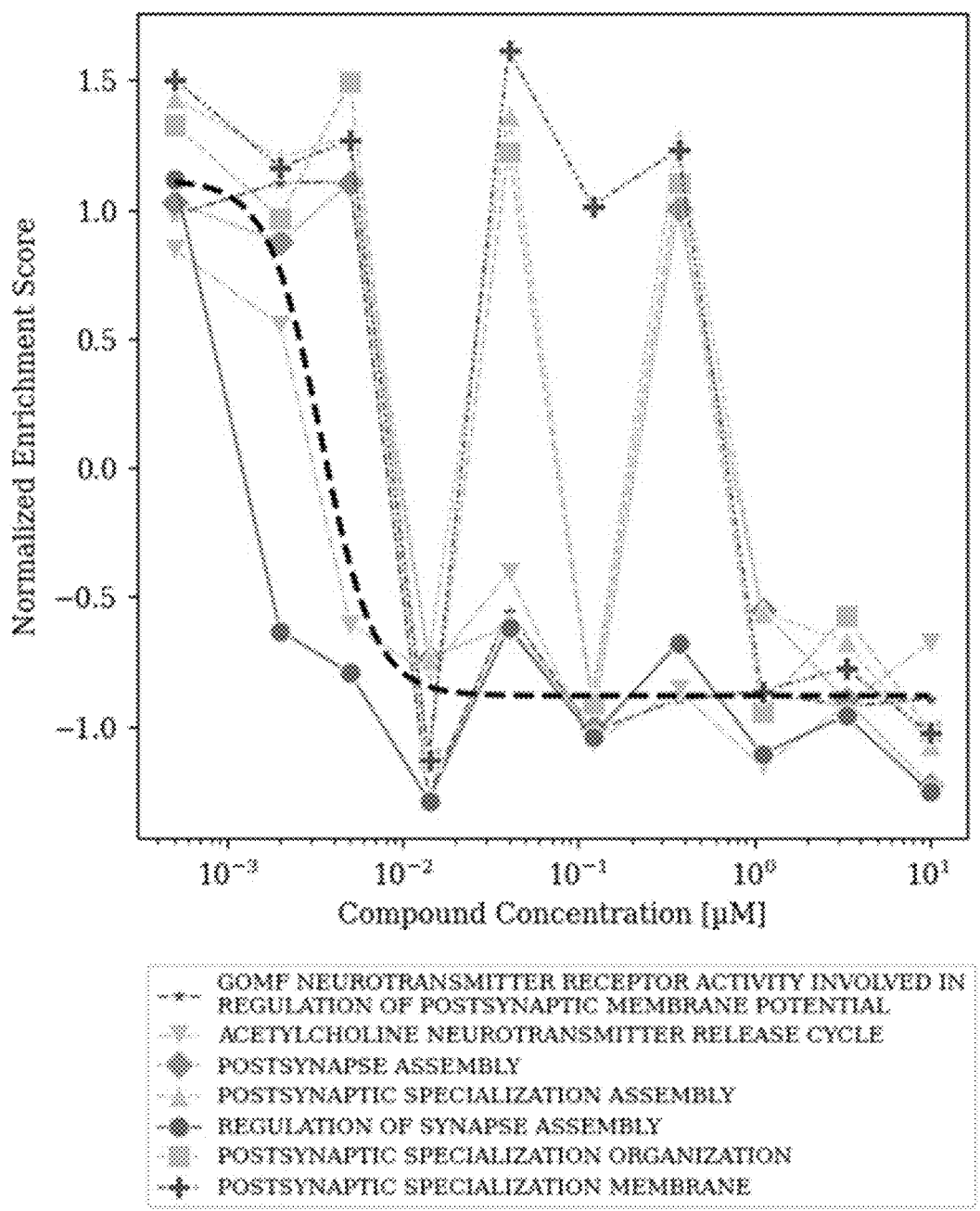
FIG. 10 depicts a dose-dependent depletion of synaptic pathways significantly affected by nortriptyline treatment in Example 5. At low concentrations, a number of synaptic pathways associated with synaptic assembly and organization were enriched in patient neurons compared to wildtype. However, at high concentrations, these pathways showed a reversal in activity signature, indicating a depletion of previously enriched pathways. Pathway dose-response curves further demonstrated a dose-dependent depletion of synaptic pathways. The EC50 of the pathway depletion response was determined to be 0.00342 μM.

At low concentrations, a number of synaptic pathways associated with synaptic assembly and organization were enriched in patient neurons compared to wildtype. However, at high concentrations, these pathways showed a reversal in activity signature, indicating a depletion of previously enriched pathways. (FIG. 10).

Pathway dose-response curves further demonstrated a dose-dependent depletion of synaptic pathways. The EC50 of the pathway depletion response was determined to be 0.00342 µM. The normalized enrichment scores of each pathway shown in FIG. 10 at each tested concentration in patient cells compared to wildtype neurons is provided in FIG. 11.

Figure 12:
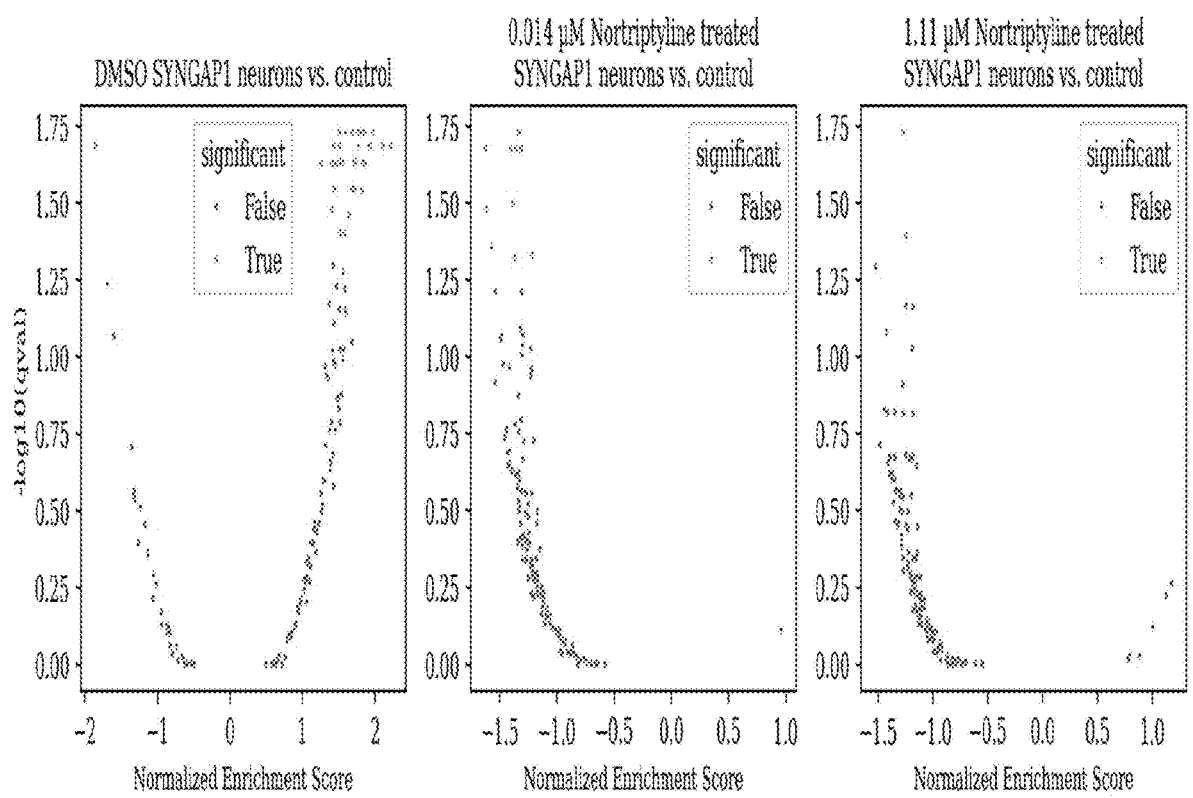
FIG. 12 shows all synaptic pathways in vehicle-control (DMSO) treated patient neurons compared to control in Example 5. The leftmost panel shows a number of enriched pathways (enrichment score >0), post nortriptyline HCl treatment all enriched pathways were depleted (enrichment score <0) (middle and right panel). A significant number of synaptic pathways show a similar trend, vehicle-control treated patient neurons show a number of enriched pathways (significant [q-value <0.1] and non-significant [q-value >0.1]). Post dosing with nortriptyline all synaptic pathways that were previously enriched were depleted.

It was observed that all synaptic pathways that were previously enriched were depleted after treatment with nortriptyline (FIG. 12).

Example 6

Syngap Neurons were differentiated for 24 days, followed by two treatments with 2 μM nortriptyline, administered every 2 days over 4 days. After treatment, cells were fixed for immunohistochemistry (IHC) and stained for SynGAP, PSD-95, and MAP2a.

Figure 13:
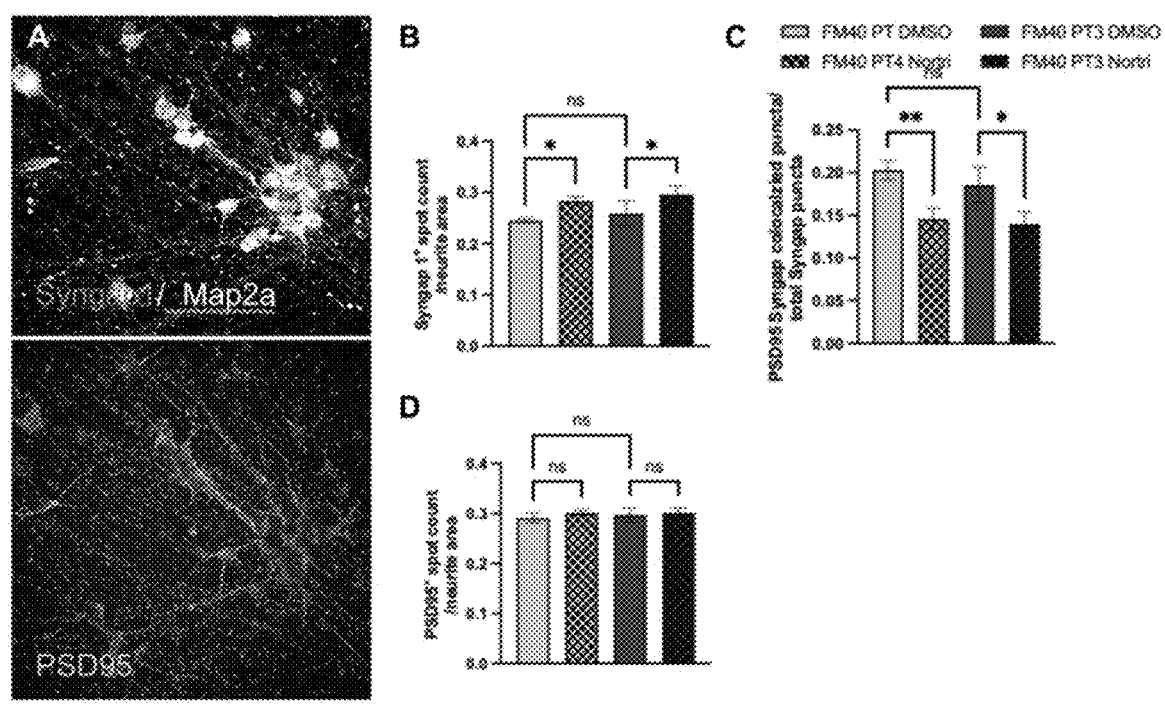
FIG. 13 shows effects of nortriptyline on SynGAP1 localization and synaptic colocalization in patient-derived Syngap neurons in Example 6. (A) Representative immunofluorescence images of SynGAP1 (magenta) and MAP2a (white, top) and PSD-95 (green, bottom) in patient-derived neurons. SynGAP1 is visualized within neuronal dendrites, while PSD-95 puncta mark excitatory synapses. (B) Quantification of SynGAP1+ spot count normalized to neurite area in different patient-derived neuronal lines (control FM40 PT4, Syngap patient FM40 PT3) treated with DMSO (control) or nortriptyline (Nortri). Nortriptyline treatment significantly increases SynGAP1 spot count, indicating enhanced SynGAP1 expression or redistribution across neuronal compartments. (C) Proportion of SynGAP1 puncta colocalized with PSD-95. Nortriptyline treatment reduces SynGAP1-PSD95 colocalization, suggesting that the drug disrupts the recruitment or retention of SynGAP1 at PSD-95-enriched excitatory synapses. (D) Since PSD-95 levels remain unchanged, nortriptyline does not alter the overall number of excitatory synapses but instead selectively affects SynGAP1 localization at these sites. Means ±Standard deviation, n=4-6, 1-way ANNOVA with Bonferroni's post-hoc test, * $p<0.5$, ** $p<0.01$, ns, not significant.

It was concluded that nortriptyline significantly increased SynGAP1 expression (increased Syngap1 puncta, FIG. 13 ((A) (top), (B)) but redistributed it away from PSD-95-enriched excitatory synapses (lower PSD95 Syngap colocalization FIG. 13 ((A) (bottom), (C)) without altering overall PSD-95 levels (unchanged PSD95-positive counts, FIG. 13D), suggesting that nortriptyline affects SynGAP1 localization rather than excitatory synapse density, potentially modifying synaptic signaling.

Example 7

A 10-year-old boy with SYNGAP1-Related Disorder was treated with NTP under the close supervision of his physician throughout treatment.

The patient received an escalating dose of NTP twice daily; dosage increased from 10 to 40 mg NTP over an 8-week period and then continued at 40 mg daily. Escitalopram (Lexipro®), a selective serotonin reuptake inhibitor (SSRI), was discontinued 1 week before starting NTP.

Figure 14:
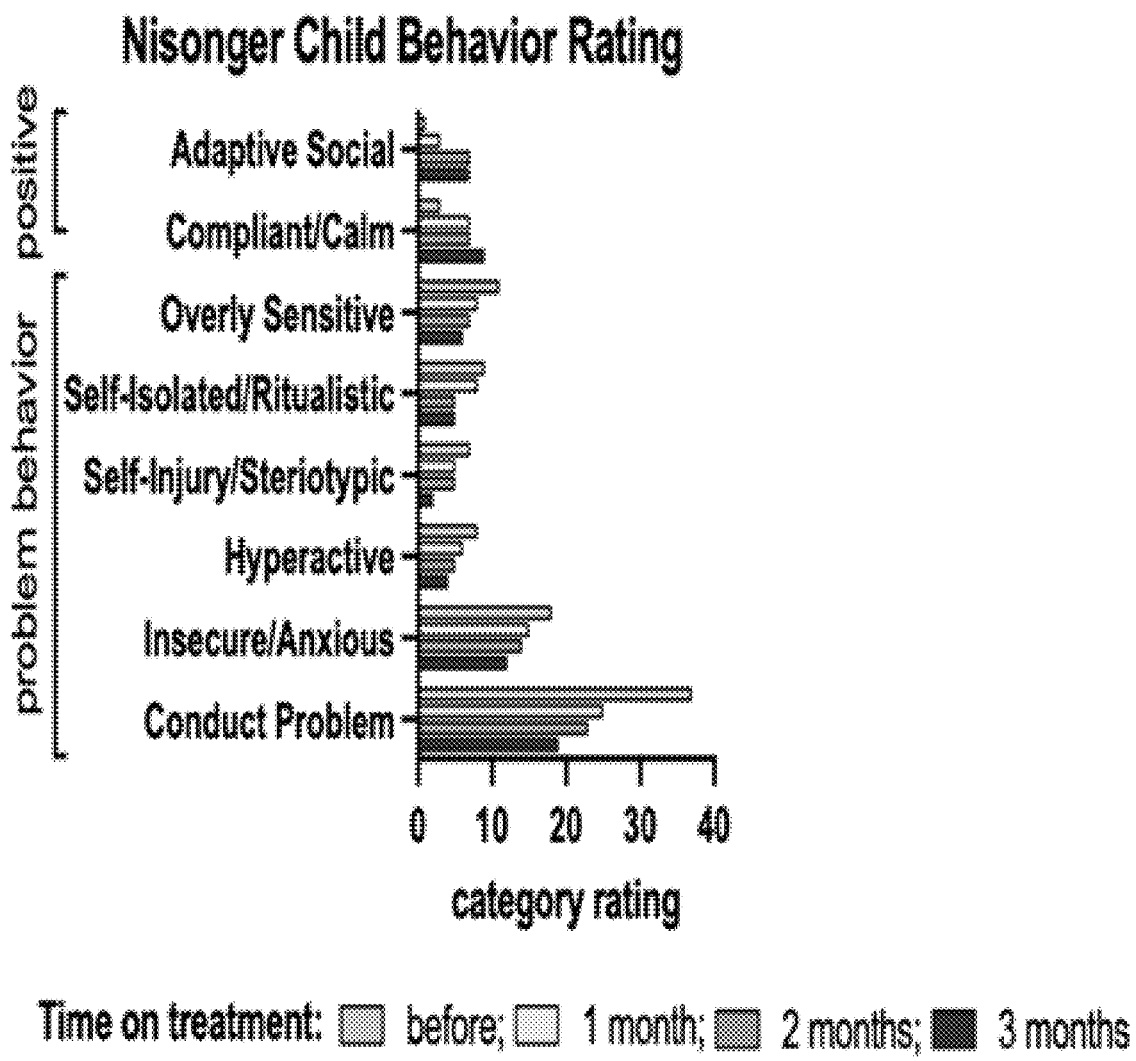
FIGS. 14A-C summarize results of standardized assessments taken before, at 1 month, 2 months and 3 months after initiation of nortriptyline (NTP) treatment of Example 7.
Figure 14:
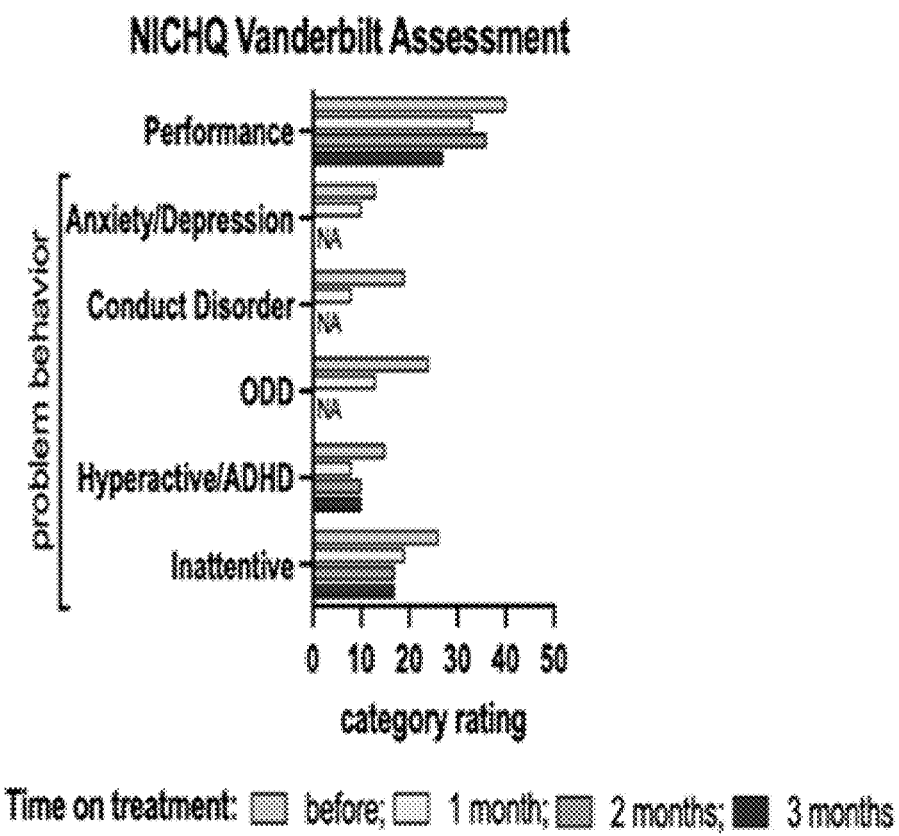
Figure 14:
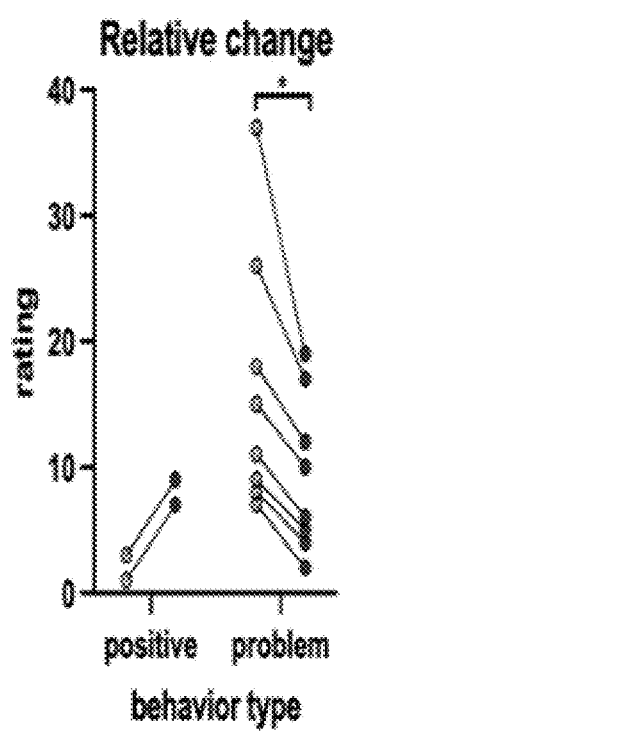

Parents recorded changes in the patient's seizures, sleep, behaviors, communication, sensory, and GI issues before and during the use of NTP for the first 12 weeks. Before and at monthly intervals for 3 months after starting NTP, the parents completed the Nisonger Child Behavior Rating Form and the National Institute for Children's Health Quality (NICHQ) Vanderbilt Assessment Scale. The assessment forms were used to rate positive and problem behaviors as listed in FIGS. 14A-C, using the instruction outlined for each assessment. FIG. 14C shows improved function by an increase in positive behaviors and decrease in problem behaviors.

The medication was generally well-tolerated, yet minor concerns were noted. Constipation and some increased obsessive behaviors were observed with escalating doses of NTP. Seizures were not reported before, or observed after, starting NTP. Improvements in problematic behaviors and communication were observed within the first week of treatment. Reduced aggressions and increased verbal communication and engagement were reported to consistently improve through week 12. Improvements in these areas were corroborated by reports from therapists and teachers. Improvements in sleep and sensory issues were also noted within the first week but did not consistently improve over time.

Parent notes on the impact of NTP during the first 12 weeks of treatment are summarized in Table 2.

| | Weeks after initiation of nortriptyline (NTP) | | | | | |
|---|---|---|---|---|---|---|
| Symptoms | Week 1<br>10 mg NTP | Week 2<br>20 mg NTP | Week 3<br>20 mg NTP | Week 4<br>30 mg NTP | Week 8<br>40 mg NTP | Week 12<br>40 mg NTP |
| Sleep | Easier to return to bed after night time wake up. | Increased dream activity. | No reported change. | No reported change. | Several night time wake ups. Self-reported nightmare. | No reported change. |
| Behaviors | No aggressions during therapy. Easier transitions. Increased patience and self control. Increased interest in using the toilet. | Reduced severity and frequency of aggressions. Less reactive; happier. | Continued reduced severity and frequency of aggressions. More calm. | Continued reduced severity and frequency of aggressions. However, some shift back to more negative moods. | Continued reduced severity and frequency of aggressions. Improved attention, cooperation and resiliency. | Continued reduced severity and frequency of aggressions. |
| Communication | Increased interest in activities, appropriate emotional expression, awareness, and depth of discussion. | Increased depth and ease of verbal communication. More engaged. | Continued increased depth, length and ease of verbal communication. | Continued increased depth, length and ease of verbal communication | Continued increased depth, length and ease of verbal communication. Increased understanding of environment and situations. | Continued increased depth, length and ease of verbal communication. |
| Sensory | Reduced picking. | Increased spatial awareness. | No reported change. | Increased obsessions. | No reported change. | Continued increased obsessions. |
| GI | No reported change. | No reported change. | Increased constipation | Complaint of stomach ache. | Improved bowel movements. | Continued constipation. |

The improvements in behaviors and communications were categorized as moderate during the first two weeks of therapy and significant during weeks 3 to 12 of therapy.

The improvements in sleep and sensory processing during weeks 1 and 2 of therapy were categorized as mild.

The improvements in GI symptoms during week 8 of therapy were categorized as mild.

It was concluded that administration of NTP improved quality of life of the patient and his caregivers. NTP appeared to be safe, well-tolerated, and effective at improving behaviors and communication in the patient. After 3 months of therapy, the patient was calmer and more compliant and showed less inattentive and maladaptive behaviors, and the parents were highly satisfied with their child's improvements and continued to include NTP in their medication regimen.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

While the invention has been disclosed with reference to specific embodiments, it is apparent that other embodiments and variations of this invention may be devised by others skilled in the art without departing from the true spirit and scope of the invention. All patents and publications cited herein are incorporated by reference in their entirety. The appended claims are intended to be construed to include all such embodiments and equivalent variations.

What is claimed is:

1. A method of treating a neurodevelopmental disorder in a subject in need thereof comprising administering to the subject a therapeutically effective amount of a drug capable of modulating SYNGAP1 gene expression in the subject,
    wherein the neurodevelopmental disorder is a synaptopathy, and
    the drug is selected from a group consisting of nortriptyline and pharmaceutically acceptable salts thereof.

2. The method of claim 1, wherein the synaptopathy is SYNGAP1-Related Disorder.

3. The method of claim 1, wherein the drug is a pharmaceutically acceptable salt of nortriptyline.

4. The method of claim 3, wherein the drug is administered orally once, twice, three times a day or four times a day.

5. The method of claim 4, wherein from about 1 mg to about 150 mg of the drug is administered per day.

6. The method of claim 5, wherein from about 1 mg to about 100 mg of the drug is administered per day.

7. The method of claim 5, wherein the drug is nortriptyline hydrochloride.

8. The method of claim 1, wherein from about 1 mg to about 100 mg of the drug is administered per day.

9. The method of claim 1, wherein the administering results in an improvement in a communication of the subject and/or an improvement in behaviors of the subject.

10. The method of claim 5, wherein the subject does not have depression.

11. A method of treating a neurodevelopmental disorder in a subject in need thereof comprising
    administering a first dose of nortriptyline or a pharmaceutically acceptable salt thereof daily to the subject for about 1 to 4 weeks, and then
    administering a second dose of nortriptyline or a pharmaceutically acceptable salt thereof daily to the subject for about 1 to 4 weeks,
    wherein the second dose is higher than the first dose,
    the first dose is from about 1 mg to about 10 mg, and
    the second dose is from about 2 mg to about 20 mg,
    wherein the neurodevelopmental disorder is a synaptopathy.

12. The method of claim 11, wherein the synaptopathy is SYNGAP1-Related Disorder.

13. The method of claim 12, wherein from about 1 mg to about 100 mg of nortriptyline or nortriptyline hydrochloride is administered per day.

14. The method of claim 11, further comprising administering, after the administering the second dose, a third dose of nortriptyline or a pharmaceutically acceptable salt thereof daily to the subject for about 1 to 4 weeks, wherein the third dose is higher than the second dose, the third dose is from about 3 mg to about 30 mg, and less than 50 mg of nortriptyline or a pharmaceutically acceptable salt is administered per day.

15. The method of claim 14, wherein the subject is a child under the age of 12.

16. A method for increasing the expression of SYNGAP1 gene in a subject in need thereof comprising administering a therapeutically effective amount of nortriptyline or a pharmaceutically acceptable salt thereof to the subject.

17. The method of claim 1, further comprising administering to the subject a therapeutically effective amount of N-acetyl-L-leucine.

18. The method of claim 16, wherein the pharmaceutically acceptable salt is nortriptyline hydrochloride.

19. The method of claim 18, wherein from about 1 mg to about 100 mg of nortriptyline hydrochloride is administered per day.

20. The method of claim 1, wherein nortriptyline or a pharmaceutically acceptable salt thereof is administered orally.

* * * * *